US012698340B2

(12) United States Patent
Satpayev et al.

(10) Patent No.: US 12,698,340 B2
(45) Date of Patent: *Aug. 4, 2026

(54) COMPOSITIONS AND METHODS REGARDING ENGINEERED AND NON-ENGINEERED γδ T-CELLS FOR TREATMENT OF SOLID TUMORS

(71) Applicant: ADICET THERAPEUTICS, INC., Redwood City, CA (US)

(72) Inventors: Daulet Kadyl Satpayev, Menlo Park, CA (US); Marissa Ann Herrman, Menlo Park, CA (US); Jason Michael Romero, Menlo Park, CA (US); Yifeng Frank Jing, Menlo Park, CA (US); Zili An, Menlo Park, CA (US); Aya Jakobovits, Menlo Park, CA (US)

(73) Assignee: ADICET THERAPEUTICS, INC., Redwood City, CA (US)

( * ) Notice: Subject to any disclaimer, the term of this patent is extended or adjusted under 35 U.S.C. 154(b) by 1231 days.

This patent is subject to a terminal disclaimer.

(21) Appl. No.: 17/281,886

(22) PCT Filed: Oct. 1, 2019

(86) PCT No.: PCT/US2019/054144
§ 371 (c)(1),
(2) Date: Mar. 31, 2021

(87) PCT Pub. No.: WO2020/072546
PCT Pub. Date: Apr. 9, 2020

(65) Prior Publication Data
US 2021/0388109 A1 Dec. 16, 2021

Related U.S. Application Data

(60) Provisional application No. 62/739,826, filed on Oct. 1, 2018.

(51) Int. Cl.
| | |
|---|---|
| *A61P 35/00* | (2006.01) |
| *A61K 38/17* | (2006.01) |
| *A61K 38/20* | (2006.01) |
| *A61K 39/395* | (2006.01) |
| *A61K 40/11* | (2025.01) |
| *A61K 40/31* | (2025.01) |
| *A61K 40/42* | (2025.01) |
| *C07K 14/54* | (2006.01) |
| *C07K 14/705* | (2006.01) |
| *C07K 16/28* | (2006.01) |

(Continued)

(52) U.S. Cl.
CPC .......... *C07K 16/303* (2013.01); *A61K 38/177* (2013.01); *A61K 38/1774* (2013.01); *A61K 38/2013* (2013.01); *A61K 38/2086* (2013.01); *A61K 39/39558* (2013.01); *A61K 40/11* (2025.01); *A61K 40/31* (2025.01); *A61K*

*40/4245* (2025.01); *A61K 40/4261* (2025.01); *A61P 35/00* (2018.01); *C07K 14/5443* (2013.01); *C07K 14/7051* (2013.01); *C07K 14/70517* (2013.01); *C07K 14/70578* (2013.01); *C07K 16/2833* (2013.01); *C07K 16/30* (2013.01); *C12N 5/0636* (2013.01); *A61K 2039/505* (2013.01); *A61K 2239/38* (2023.05); *A61K 2239/53* (2023.05); *A61K 2239/57* (2023.05); *C07K 2317/565* (2013.01); *C07K 2317/73* (2013.01); *C07K 2317/74* (2013.01); *C07K 2319/02* (2013.01); *C07K 2319/03* (2013.01); *C07K 2319/30* (2013.01); *C07K 2319/33* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 7,728,114 B2 * | 6/2010 | Mach | A61P 1/04 |
| | | | 530/388.22 |
| 9,539,251 B2 | 1/2017 | Sampath et al. | |

(Continued)

FOREIGN PATENT DOCUMENTS

| | | | |
|---|---|---|---|
| CN | 103833852 A | * | 6/2014 |
| CN | 104087607 A | | 10/2014 |

(Continued)

OTHER PUBLICATIONS

Dwyer et al., Fueling Cancer Immunotherapy With Common Gamma Chain Cytokines, Front. Immunol. 10:263, 18 pages, Feb. 2019.*

(Continued)

*Primary Examiner* — Zachary S Skelding
(74) *Attorney, Agent, or Firm* — Todd Lorenz

(57) ABSTRACT

Aspects of the invention include compositions and methods for treatment of solid tumors with engineered or non-engineered γδ-T cells. In some embodiments, the γδ-T cells comprise a chimeric antigen receptor (CAR) construct. The CAR construct can contain an anti-TryD binding domain, a CD8α hinge and transmembrane domain, a costimulatory domain, a 003ζ signalling domain, a combination thereof, or all thereof. The CAR construct can contain an anti-GPC3 binding domain, a CD8α hinge and transmembrane domain, a costimulatmy domain, a CD3ζ signalling domain, a combination thereof, or all thereof. The CAR construct can contain a domain encoding for a secreted common gamma chain cytokine such as a sIL 15 domain.

36 Claims, 7 Drawing Sheets
Specification includes a Sequence Listing.

(51) Int. Cl.

| | | |
|---|---|---|
| *C07K 16/30* | (2006.01) | |
| *C12N 5/0783* | (2010.01) | |
| *A61K 39/00* | (2006.01) | |

(56) References Cited

U.S. PATENT DOCUMENTS

| | | | |
|---|---|---|---|
| 2004/0167319 A1 | 8/2004 | Teeling et al. | |
| 2009/0035322 A1 | 2/2009 | Martin et al. | |
| 2016/0046724 A1 | 2/2016 | Brogdon et al. | |
| 2016/0175358 A1* | 6/2016 | Jakobovits | C12N 15/00 |
| | | | 435/372.3 |
| 2018/0125889 A1 | 5/2018 | Leek et al. | |
| 2019/0046659 A1* | 2/2019 | Wang | A61K 47/6879 |
| 2020/0289561 A1* | 9/2020 | Qian | C12N 15/8206 |
| 2021/0094994 A1* | 4/2021 | Heczey | C07K 14/7051 |
| 2021/0154231 A1 | 5/2021 | Li et al. | |
| 2021/0252056 A1* | 8/2021 | Metelitsa | C12N 5/0646 |
| 2021/0363245 A1 | 11/2021 | Kochenderfer et al. | |
| 2023/0071098 A1* | 3/2023 | Tamada | C07K 14/70521 |

FOREIGN PATENT DOCUMENTS

| | | | | |
|---|---|---|---|---|
| JP | 2018-512161 A | 5/2018 | | |
| WO | WO 2006130458 A2 | 12/2006 | | |
| WO | WO 2009/018411 A1 | 2/2009 | | |
| WO | WO 2016034666 A1 | 3/2016 | | |
| WO | WO 2016138491 A1 | 9/2016 | | |
| WO | WO 2016139487 A1 | 9/2016 | | |
| WO | WO 2016166544 A1 | 10/2016 | | |
| WO | WO 2016/199140 A1 | 12/2016 | | |
| WO | WO 2016/199141 A2 | 12/2016 | | |
| WO | WO 2016/201394 A1 | 12/2016 | | |
| WO | WO 2017/147383 A1 | 8/2017 | | |
| WO | WO 2017/197347 A1 | 11/2017 | | |
| WO | WO 2018/019772 A1 | 2/2018 | | |
| WO | WO 2018/085690 A1 | 5/2018 | | |
| WO | WO 2018/087557 A1 | 5/2018 | | |
| WO | WO 2018/098365 A1 | 5/2018 | | |
| WO | WO 2018/131586 A1 | 7/2018 | | |
| WO | WO 2018/138522 A1 | 8/2018 | | |
| WO | WO 2018/147805 A1 | 8/2018 | | |
| WO | WO-2018200586 A1 * | 11/2018 | ....... | G01N 33/57525 |
| WO | WO 2018/229530 A1 | 12/2018 | | |

OTHER PUBLICATIONS

Fan, M., Plasmids 101_ Multicistronic Vectors, Retreived onine from <URL:https://blog.addgene.org/plasmids-101-multicistronic-vectors> [retreived on Mar. 27, 2024), 9, Sep. 2014.*

Shimizu et al. (Front. Oncol. 9:248. (Apr. 10, 2019)). (Year: 2019).*

Nishida et al. (Cancers (Basel). Sep. 10, 2019;11(9):1339). (Year: 2019).*

Almeida et al. (Cancer Res; 22(23); 5795-804, and supplemental pp. 1-15 (2016)). (Year: 2016).*

Capsomidis et al. (Molecular therapy: the journal of the American Society of Gene Therapy, 26(2), 354-365, 2017). (Year: 2017).*

Cordova et al. (PLoS One 7(11): e49878 (2012)). (Year: 2012).*

Kenna et al. (Clinical Immunology 113 (2004) 56-63). (Year: 2004).*

Harlow et al. (Antibodies, A Laboratory Manual, Cold Spring Harbor laboratory, 1988, pp. 37-47. (Year: 1988).*

Edwards et al. (J. Mol. Biol. (2003) 334, 103-118). (Year: 2003).*

Lloyd et al. (Protein Engineering, Design & Selection vol. 22 No. 3 pp. 159-168, 2009). (Year: 2009).*

Fisher et al., Clin. Cancer Res. 20, 5720-5732 (2014). (Year: 2014).*

Nakano et al. (Anti-Cancer Drugs 2010, 21:907-916). (Year: 2010).*

English language Google Patents translation of CN103833852A, pp. 1-30, obtained Mar. 2026. (Year: 2026).*

Gao et al. (Clin Cancer Res; 20(24); 6418-28 (2014) further including Supplementary Tables, Materials and Methods, and Figures pp. 1-16). (Year: 2014).*

Alabanza et al., "Function of Novel Anti-CD19 Chimeric Antigen Receptors with Human Variable Regions is Affected by Hinge and Transmembrane Domains", Molecular Therapy: the Journal of the American Society of Gene Therapy, vol. 25, No. 11, pp. 2452-2465 (2017).

Chmielewski et al., "TRUCKs: the fourth generation of CARs", Expert Opinion on Biological Therapy, vol. 15, No. 8, pp. 1145-1154 (2015).

Deniger et al., "Bispecific T-cells Expressing Polyclonal Repertoire of Endogenous [gamma][delta] T-cell Receptors and Introduced CD19-specific Chimeric Antigen Receptor", Molecular Therapy : The Journal of the American Society of Gene Therapy, vol. 21, No. 3, p. 638-647 (2013).

Fisher et al., "Engineering Approaches in Human Gamma Delta T Cells for Cancer Immunotherapy", Frontiers in Immunology, vol. 9, (2018).

Lamb et al., "Clinical-scale manufacturing of γδ T cells for protection against infection and disease recurrence following haploidentical peripheral blood stem cell transplantation and cyclophosphamide gvhd prophylaxis", Bone Marrow Transplantation, vol. 53, pp. 766-769 (2018).

Liu et al., "Targeting Alpha-Fetoprotein (AFP)-MHC Complex with CAR T-Cell Therapy for Liver Cancer", Clinical Cancer Research, vol. 23, No. 2, pp. 478-488 (2017).

Markley et al., "IL-7 and IL-21 are superior to IL-2 and IL-15 in promoting human T cell-mediated rejection of systemic lymphoma in immunodeficient mice", Blood, vol. 115, No. 17, p. 3508-3519 (2010).

Rafiq et al., "Optimized T-cell receptor-mimic chimeric antigen receptor T cells directed toward the intracellular Wilms Tumor 1 antigen", Leukemia, vol. 31, No. 8, pp. 1788-1797 (2017).

Ribot et al., "Searching for "signal 2": costimulation requirements of γδ T cells", Cell. Mol. Life Sci. (2011) 68:2345-2355.

Siegers et al., "Human Vδ1 γδ T cells expanded from peripheral blood exhibit specific cytotoxicity against B-cell chronic lymphocytic leukemia-derived cells", Cytotherapy, vol. 13, pp. 753-764 (2011).

Tassev, D.V., "Generation and Use of HLA-A2-Restricted, Peptide-Specific Monoclonal Antibodies and Chimeric Antigen Receptors", May 1, 2011; Retrieved from the Internet: URL:https://www.sloankettering.edu/sites/default/files/node/165658/document/final-dimiter-tassev.pdf.

Klein et al. "Epitope interaction of monoclonal antibodies targeting CD20 and their relationship to functional properties", mAbs, vol. 5:1, pp. 22-33 (2013).

Meyer et al. "New insights in Type I and II CD20 antibody mechanisms-of-action with a panel of novel CD20 antibodies", British Journal of Haematology, vol. 180, pp. 808-820 (2018).

Somasundaram et al., "Tumor-associate B-cells induce tumor heterogeneity and therapy resistance", Nature Communications, vol. 8:607, pp. 1-20 (2017).

* cited by examiner

Fig. 4

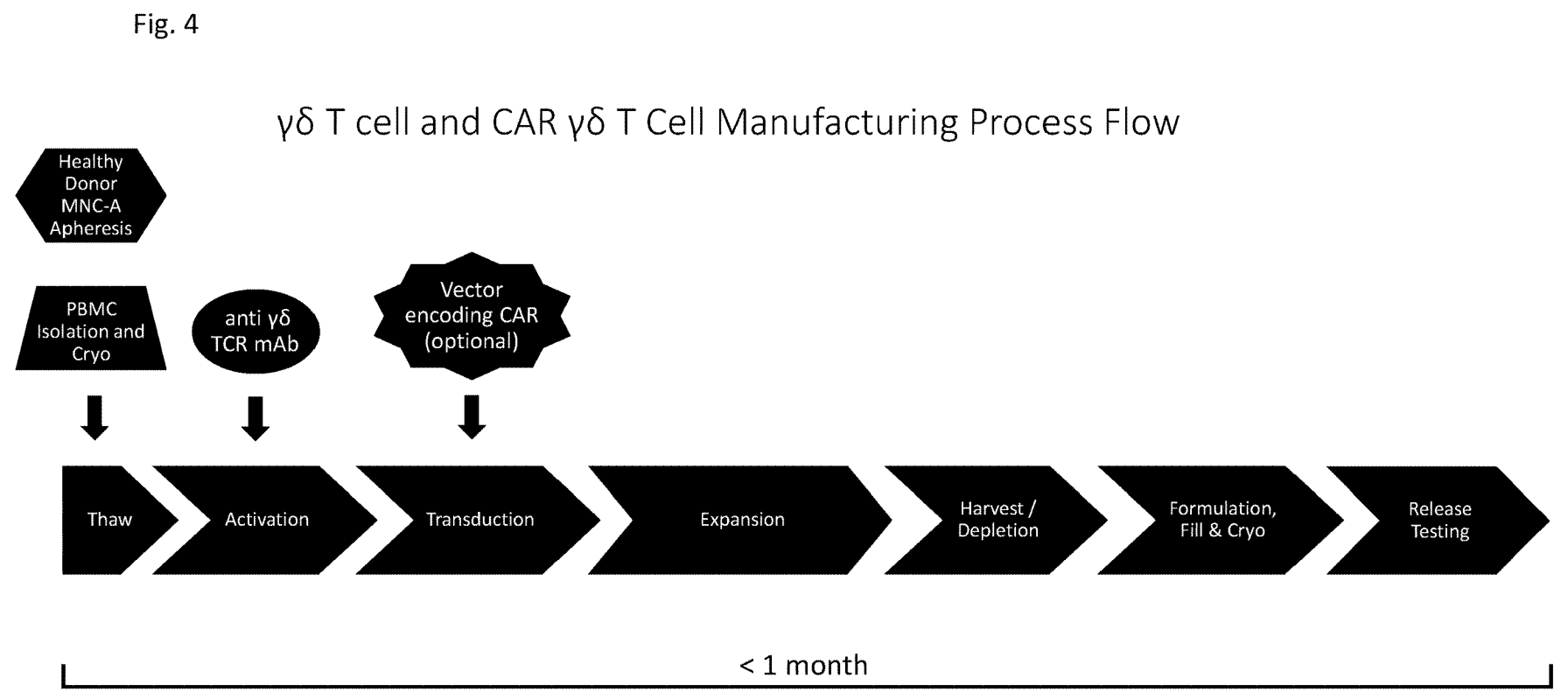

γδ T cell and CAR γδ T Cell Manufacturing Process Flow

Healthy Donor MNC-A Apheresis

PBMC Isolation and Cryo anti γδ TCR mAb

Vector encoding CAR (optional)

Thaw

Activation

Transduction

Expansion

Harvest / Depletion

Formulation, Fill & Cryo

Release Testing

< 1 month

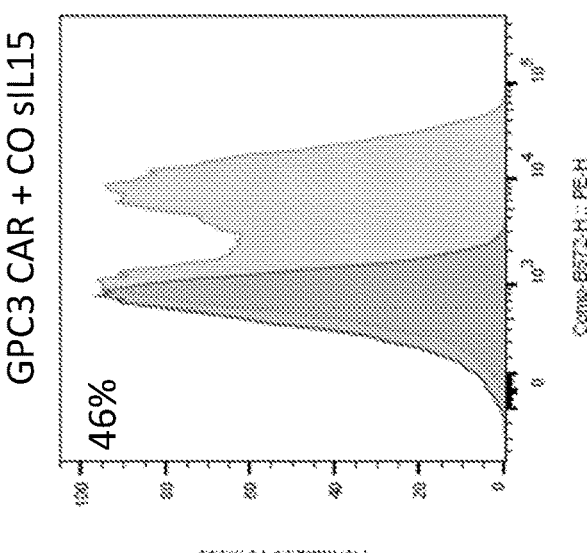
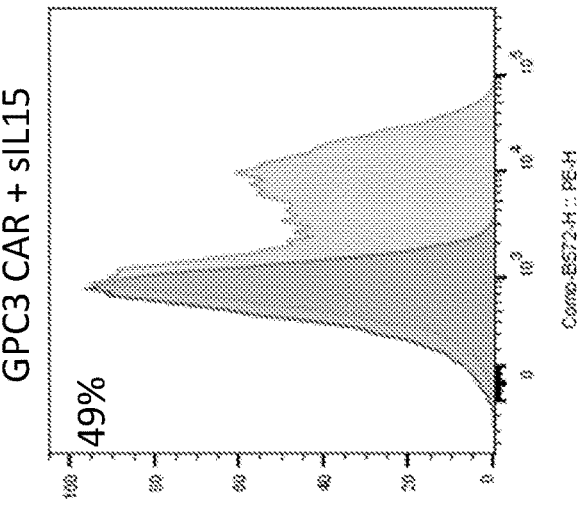
Fig. 6
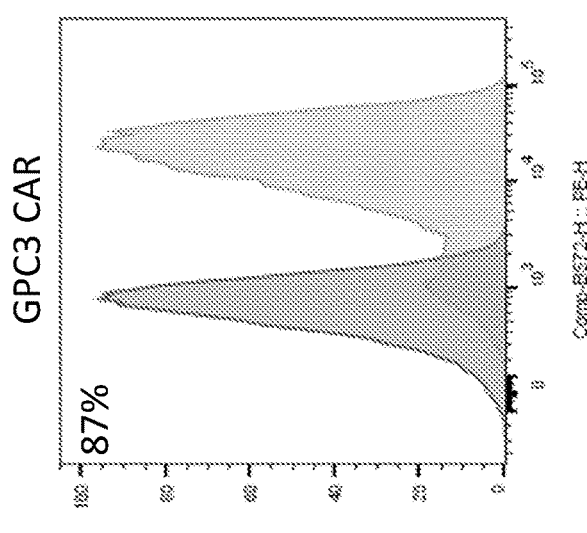

PLC/PRF/5-Rluc (18 hr)

- Untransduced γδ T cells
- GPC3 CAR
- GPC3 CAR + sIL-15
- GPC3 CAR + CO sIL-15

HepG2-Rluc (18 hr)

Hep3B-Rluc (18 hr)

COMPOSITIONS AND METHODS REGARDING ENGINEERED AND NON-ENGINEERED γδ T-CELLS FOR TREATMENT OF SOLID TUMORS

CROSS-REFERENCES TO RELATED APPLICATIONS

This application claims the benefit of priority to U.S. Provisional Application No. 62/739,826, filed Oct. 1, 2018, the contents of which are hereby incorporated for any and all purposes.

SEQUENCE LISTING

The instant application contains a Sequence Listing which has been submitted electronically in ASCII format and is hereby incorporated by reference in its entirety. Said ASCII copy, created on Jan. 8, 2020, is named ADC-0006-PCT-_SL.txt and is 48,406 bytes in size.

BACKGROUND OF THE INVENTION

Adoptive cellular therapy has undergone near constant iteration for more than thirty (30) years, from early days focusing on basic lymphokine activation and/or tumor infiltration to more recent strategies engineering these immune cells to express genetically engineered antigen receptors, such as chimeric antigen receptors (CARs)s. While there have been some hints and indications of the curative potential of these approaches along the way, much still remains to be done. In particular, successful tumor eradication by CAR-T lymphocytes depends on CAR-T cell persistence and effector function, but an excess of either can trigger graft-versus-host effects in the patient. Moreover, solid tissues in particular present a problem due to the lack of available positive stimulation and the presence of an inhibitory environment. As such the art is testing myriad co-stimulation strategies in both T and NK cells, and in αβ T cells in particular, with a view to balancing efficacy with safety. Notably, the practical translation of any of these various approaches to γδ T cells is at best uncertain, given the current lack of understanding around the co-stimulation requirements of γδ T cells as compared to αβ T cells. See, e.g., Ribot et al., "Searching for "signal 2": costimulation requirements of γδ T cells", *Cell Mol. Life Sci.* (2011) 68:2345-2355.

Accordingly, improved strategies are still needed to improve the specificity or selectivity of the cells, to improve safety of the cells, for example by reducing or avoiding graft versus host (GVH) effects, to improve efficacy of the cells against solid tumor cells, for example, by avoiding suppression of effector functions, and to improve the activity and/or survival of the cells upon administration to subjects. Provided are methods, cells, compositions, kits, and systems that meet such needs.

SUMMARY OF INVENTION

Aspects of the invention include an isolated nucleic acid sequence encoding a chimeric antigen receptor (CAR), wherein the CAR comprises a binding domain that specifically binds to a protein-peptide complex comprising a tumor associated antigen (TAA) peptide and an MHC protein, wherein the complex is expressed on a surface of a solid tumor cell, optionally wherein the binding domain binds the complex in an HLA restricted manner, a CD8α hinge domain; a Mkt transmembrane domain; a costimulatory signaling region selected from a 4-1BB costimulatory signaling region and a CD27 costimulatory signaling region: and a CD3ζ signalling domain. Aspects of the invention further include a non-engineered γδ T cell described herein and an engineered γδ T cell comprising a nucleic acid encoding a CAR construct described herein, wherein the γδ T cell functionally expresses the nucleic acid encoded CAR on the surface of the γδ T cell.

Aspects of the invention further include a plurality of γδ T cells as described herein. Aspects of the invention further include a method of making the γδ T cell or plurality of γδ T cells described herein. Aspects of the invention further include a pharmaceutical composition comprising a pharmaceutically acceptable excipient and a γδ T cell or plurality of γδ T cells described herein. Aspects of the invention further include contacting a solid tumor cell with a tumor cell killing effective amount of a γδ T cell as described herein or plurality of γδ T cells described herein.

In one aspect, the present invention provides an isolated nucleic acid sequence encoding a chimeric antigen receptor (CAR), wherein the CAR comprises (a) a binding domain that specifically binds to a protein-peptide complex comprising a tumor associated antigen (TAA) peptide and an MHC protein, wherein the complex is expressed on a surface of a solid tumor cell, optionally wherein the binding domain binds the complex in an HLA restricted manner; (b) a hinge domain, such as a CD8α, hinge domain; (c) a transmembrane domain, such as a CD8α transmembrane domain; (d) a costimulatory signaling region or combination of costimulatory signaling regions, optionally wherein the costimulatory signaling region(s) are selected from a 4-1BB (CD137) costimulatory signaling region and a CD27 costimulatory signaling region; and (e) a signaling domain, such as a CD3ζ signaling domain, In some embodiments, the foregoing elements (a)-(e) are encoded OR the sense strand of the isolated nucleic acid in 5' to 3' order.

In some embodiments, the TAA comprises a contiguous region of TyrD, in some embodiments, the contiguous region of TyrD comprises at least, or at least about, 4 and no more than, or no more than about, 12 contiguous amino acids of TyrD, preferably, or preferably about, 7, 8, or 9 contiguous amino acids of TyrD. In some embodiments, the contiguous region of TyrD is $TyrD_{369-377}$. In some embodiments, the binding domain that specifically binds the TAA peptide MEW complex specifically binds $HEA-A2/TyrD_{369-377}$.

In some embodiments, the binding domain specifically hinds to the epitope bound by, or competes with, an antibody comprising: a CDRH1 comprising TSGMGVS (SEQ ID NO: 33); a CDRH2 comprising HIYWDDDKRYNPSLKS (SEQ ID NO: 34); a CDRH3 comprising KDYGSSFY-AMHY (SEQ ID NO: 35); a CDRL1 comprising KASQ-DIHNYIA (SEQ ID NO: 36); a CDRL1 comprising YTS-TIQP (SEQ ID NO: 37); and a CDRL2 comprising LQYDNLWT (SEQ ID NO: 38).

In another aspect, the binding domain specifically binds to a tumor associated antigen (TAA) expressed on a surface of a solid tumor cell, optionally wherein the antigen is a protein-peptide complex, wherein the protein is an MHC protein, wherein the binding domain binds the protein-peptide complex in an HLA restricted manner, and the encoded CAR of the isolated nucleic acid sequence comprises (b) a hinge domain, such as a CD8α hinge domain; (c) a transmembrane domain, such as a CD8α transmembrane domain; (d) a costimulatory signaling region or combination of costimulatory signaling regions, optionally wherein the costimulatory signaling region(s) are selected from a 4-1BB (CD137) costimulatory signaling region and a CD27 costimulatory signaling region; and (e) a signaling domain, such as a CD3ζ signaling domain. In some embodiments, the foregoing elements (a)-(e) are encoded on the sense strand of the isolated nucleic acid in 5' to 3' order.

In some embodiments the binding domain specifically binds an epitope within GPC3 expressed on the surface of a solid tumor cell. In some embodiments, the binding domain comprises the following complementarity determining regions (CDRs) binds the same GPC3 epitope as an antibody comprising the following CDRs, and/or competes for binding to an epitope of GPC3 with an antibody comprising the following CDRs: a CDRH1 comprising a sequence of DYEMH (SEQ ID NO: 39) (or GYTFTDYEMH (SEQ ID NO: 40)); a CDRH2 comprising a sequence of ALDPKTGDTAYSQKFKG (SEQ ID NO: 41); a CDRH3 comprising a sequence of FYSYTY (SEQ ID NO: 42); a CDRL1 comprising a sequence of RSSQSLVHSNRNTYLH (SEQ ID NO: 43); a CDRL2 comprising a sequence of KVSNRFS (SEQ ID NO: 44); and/or a CDRL3 comprising a sequence of SQNTHVPPT (SEQ ID NO: 45).

In some embodiments of any one of the foregoing aspects or embodiments or any of the CAR encoding nucleic acids described herein, the encoded CAR comprises: a CD8α hinge domain comprising SEQ ID NO: 1 (PIPAPTIA-SQPLSLRPEACRPAAGGAVHTRGLDFACDIY) or SEQ ID NO:2 (TTTPAPRPPTPAPTIASQPLSLRPEACR-PAAGGAVHTRGLDFACDIY); or a CD8α transmembrane domain comprising SEQ ID NO:3 (IWAPLAGTCGVLLLSLVITLYC); and/or a CD3ζ signaling domain. In some cases, the CD3ζ signaling domain comprises the sequence of SEQ ID NO:4 (RVKFSRSADA-PAYQQGQNQLYNELNLGRREEYDVLDKRR-GRDPRMG GKPQRRKNPQEGLYNELQKDKMAEAY-SEIGMKGERRRGKGHDGLYQGLSTATKDTYD ALHMQALPPR); or SEQ ID NO:5 (RVKFSRSADAPA-YQQGQNQLYNELNLGRREEYD VLDKRR-GRDPEMGGKPRRKNPQEGLYNELQKDKMAEAYSEI-GMKGERRRGKGHDGL YQGLSTATKDTYDALHMQALPPR).

In some embodiments, the CAR comprises a 4-1BB costimulatory signaling region comprising SEQ ID NO:6 (KRGRKKLLY-IFKQPFMRPVQTTQEEDGCSCRFPEEEEGGCEL); or a CD27 costimulatory signaling region comprising SEQ ID NO:7. (QRRKYRSNKGESPVEPAEPCHYSCPREEEG-STIPIQEDYRKPEPACSP), or the isolated nucleic acid encodes the 4-1BB costimulatory signaling region comprising SEQ 1D NO:6 and the CD27 costimulatory signaling region comprising SEQ NO:7.

In some embodiments of any one of the foregoing, or as described herein, the isolated nucleic acid further encodes a secreted cytokine; or a secreted common gamma chain interleukin; or a secreted common gamma chain interleukin such as IL-15, preferably wherein the secreted common gamma chain interleukin such as IL-15 comprises an inter-leukin polypeptide sequence operably linked to a secretion signal sequence (e.g., a secretion signal of SEQ ID NO: 12 or 26). In some embodiments, the isolated nucleic acid encodes a secreted IL-15, preferably wherein the IL-15 comprises the sequence of SEQ ID NO:14, more preferably wherein the IL-15 comprises the sequence of 14 operably linked to a secretion signal sequence of SEQ ID NO:12, or wherein the IL-15 comprises the sequence of SEQ ID NO: 14 operably linked to a secretion signal sequence of SEQ ID NO: 26. In some cases, the secreted cytokine, common gamma chain interleukin, and/or IL-15 are encoded carboxy terminal to the binding region, hinge and transmembrane domains, signaling domain, and/or costimulation endodo-main. In some cases, the secreted cytokine, common gamma chain interleukin, and/or IL-15 are encoded on the sense strand 3' of the region encoding the binding region, hinge and transmembrane domains, signaling domain, and/or costimulation endodomain.

In some embodiments, the nucleic acid encodes a multi-cistronic linker region configured to facilitate translation of the CAR and the secreted cytokine, common gamma chain cytokine, or IL-15 as separate polypeptides. In some embodiments, the multi-cistronic linker region encodes a self cleavage and/or a cleavage polypeptide sequence. In some cases, the self-cleavage sequence is a P2A, F2A, T2A, or E2A self cleavage sequence. In some cases, the cleavage sequence is a furin cleavage sequence. In some cases, the cleavage sequence (e.g., furin cleavage sequence) is amino terminal to a self cleavage sequence. In some embodiments, the multi-cistronic linker region encodes an internal ribo-some entry site. In some embodiments, the nucleic acid encodes a multi-cistronic linker region amino terminal to the interleukin or cytokine or interleukin or cytokine secretion signal, preferably wherein the multicistronic linker region comprises a sequence of any one of SEQ ID NOs: 15-17, 25, or 27-30, or a combination thereof, or encodes an internal ribosome entry site, e.g., SEQ ID NO: 31 or 32.

In some embodiments, the secretion signal comprises a sequence of SEQ ID NO: 12 or SEQ ID NO: 26, preferably SEQ ID NO:12; and/or the sIL15 domain comprises a sequence of SEQ ID NO: 14; and/or the P2A cleavage sequence comprises a sequence of SEQ ID NO: 15 or SEQ ID NO:25; and/or the furin cleavage sequence comprises a sequence of SEQ ID NO: 16; and/or the CAR comprises, in amino to carboxy order, a sequence of SEQ ID NO: 17, SEQ ID NO: 12, and SEQ ID NO: 14.

In some embodiments, the binding domain specifically binds to HLA-A2/TyrD$_{369-377}$ and the nucleic acid encodes SEQ ID NO: 8, or SEQ ID NO: 18. in some embodiments, the binding domain specifically binds to GPC3 and the nucleic acid encodes SEQ ID NO: 20, or 22. in some embodiments, the nucleic acid comprises the sequence of SEQ ID NO: 9, SEQ ID NO: 19, SEQ ID NO: 21, 23, or 24.

In another aspect, the present invention provides a poly-peptide comprising a CAR binding domain, such as one of the polypeptides encoded by any one of the foregoing nucleic acids, or a polypeptide described herein.

In another aspect, the present invention provides an, e.g., γδ, T cell comprising the foregoing polypeptide, or com-prising a nucleic acid encoding a CAR described herein, wherein the cell functionally expresses the a binding domain of the polypeptide or nucleic acid encoded CAR on the surface of the cell. In some embodiments, the cell exhibits in vitro and/or in vivo cell killing activity against a solid tumor cell that exhibits cell surface expression of the tumor associated antigen (TAA). In some embodiments, the solid tumor cell killing activity of said cell is greater than an innate level of in vitro and/or in vivo solid tumor cell killing activity in a control cell that does not comprise a CAR construct. In some embodiments, the cell exhibits the increased solid tumor cell killing activity against HLA class I$^+$ solid tumor cells. In some embodiments, the solid tumor cell killing activity or increased solid tumor cell killing activity persists for, for about, for at least, or for at least about, 6 days to 180 days after first contact with the solid tumor cell.

In some embodiments, the cell proliferates in response to contact with a solid tumor cell that exhibits cell surface expression of the tumor associated antigen (TAA). In some embodiments, the cell exhibits increased proliferation in response to contact with a solid tumor cell that exhibits cell surface expression of the tumor associated antigen (TAA) as compared to a control cell that does not functionally express the nucleic acid encoded CAR on the surface of the cell. In some embodiments, the cell proliferates in a host organism that comprises the solid tumor cell that exhibits cell surface expression of the tumor associated antigen (TAA). In some embodiments, the cell proliferation or increased cell proliferation persists for, for about, for at least, or for at least about, 6 days to 180 days after first contact with the solid tumor cell. In some embodiments, the cell expresses one or more pro-inflammatory cytokines, optionally wherein the one or more pro-inflammatory cytokines comprises tumor necrosis factor alpha or interferon gamma, after contact with the solid tumor cell, preferably in an amount greater than a control cell that does not functionally express the nucleic acid encoded CAR on the surface of the cell.

In some embodiments, the cell exhibits reduced, substantially reduced, essentially none, or no graft versus host response when introduced into an allogeneic host in comparison to a graft versus host response exhibited by an αβ T cell administered to an allogeneic host. In some embodiments, the, e.g., γδ, T cell exhibits reduced, substantially reduced, essentially no, or no graft versus host response when introduced into an allogeneic host in comparison to a graft versus host response exhibited by an αβ T cell administered to an allogeneic host. In some embodiments, the T cell is a γ T cell. In some embodiments, the T cell is a δ T cell. In some embodiments, the T cell is a γδ T cell. In some embodiments. the T cell is a δ1, a δ2, a δ3, or a δ4 T cell, preferably a δ2⁻ δ T cell, more preferably a δ1 δ T cell. In some embodiments, the T cell is a δ1, a δ2, a δ3, or a δ4 γδ T cell, preferably a δ2⁻γδ T cell, more preferably a δ1 γδ T cell.

In another aspect, the present invention provides a plurality of of any one of the foregoing cells such as, e.g., γδ, T cells, or a plurality of cells such as, e.g., γδ, T cells as described. herein. In some embodiments, the plurality comprises at least about $10^8$ cells such as $10^8$, e.g., γδ, T cells, preferably from about $10^8$ cells, e.g., γδ, T cells to about $10^{11}$ cells, e.g., γδ, T cells. In some embodiments, the plurality comprises a composition that is at least 60%, 80%, or from about 60% or 80% to about 90% or 95% δ1, δ2, δ3, or δ4 cells, such as, e.g., γδ T cells, preferably δ1 or δ2 γδ T cells, more preferably δ2⁻ γδ T cells, most preferably δ1 γδ T cells.

In some embodiments, the present invention provides a method of making a cell, such as an, e.g., γδ, T cell as described herein, or a plurality of cells, such as, e.g., γδ, T cells as described herein, wherein the method comprises transfecting the cell(s) with a construct comprising an isolated nucleic acid sequence as described herein. In some cases, the method comprises, e.g., gamma, retroviral transduction. In some cases, the method comprises ex vivo expansion of the cell(s), wherein the ex viva expansion is performed before transfection and/or after transfection of the isolated nucleic acid sequence. In some cases, the method comprises ex viva expansion of the cell(s), wherein the ex vivo expansion is performed before transfection and after transfection of the isolated nucleic acid sequence. In some cases, the method comprises ex viva expansion of the cell(s), wherein the ex vivo expansion is performed after transfection of the isolated nucleic acid sequence. in some embodiments, the method comprises producing the from about $10^8$ cells, such as, e.g., γδ, T cells to about $10^{11}$ cells, such as, e.g., γδ, T cells that functionally express a CAR described herein within about 30 days of transfection.

In another aspect, the present invention provides a pharmaceutical composition comprising a pharmaceutically acceptable excipient and a cell or plurality of cells as described herein, such as, e.g., γδ, T cell(s) described herein.

In another aspect, the present invention provides a method of killing a solid tumor cell, the method comprising contacting the solid tumor cell with a tumor cell killing effective amount of any one of the foregoing cells or plurality of cells or pharmaceutical compositions, or a cell or plurality of cells or pharmaceutical composition as described herein. In some cases, the cell or plurality of cells are, e.g., γδ, T cell(s).

In some embodiments, the method comprises introducing a therapeutically effective amount of the cells such as, e.g., γδ, T cells) or the pharmaceutical composition into a host organism comprising the solid tumor cell. In some embodiments, the method comprises introducing into a host organism comprising the solid tumor cell a therapeutically effective amount of the cells, such as, e.g., γδ, T cell(s), or a pharmaceutical composition. thereof and simultaneously or sequentially administering one or more methods to elevate common gamma chain cytokine(s).

In some embodiments, the administering one or more methods to elevate common gamma chain cytokine(s) comprises administering simultaneously with introducing the cell(s) or sequentially an amount of common gamma chain crokine(s) effective to increase proliferation, cytotoxic activity, persistence, or the combination thereof of the introduced cell(s), preferably wherein the method comprises administering IL-2, more preferably wherein the method comprises administering IL-15. In some embodiments, the one or more methods to elevate common gamma chain cytokine(s) comprise administering an amount of common gamma chain cytokine(s) effective to increase proliferation, cytotoxic activity, persistence, or the combination thereof of the introduced cell(s) before and/or after introducing the cell(s).

In some embodiments, the one or more methods to elevate common gamma chain cytokine(s) comprises lymphodepletion before introducing the γδ cell(s). In some embodiments, the one or more methods to elevate common gamma chain cytokine(s) comprises secretion of one or more common gamma chain cytokine(s) from the introduced. cell(s), in some embodiments, the method reduces the in vivo tumor burden in the host organism, and/or increases the mean survival time of the host organism as compared to a control organism, wherein the control organism is not treated with the cell(s) or the pharmaceutical composition. In some embodiments, the method is a method of treating cancer in a subject in need thereof.

In another aspect, the present invention provides a use of a tumor cell killing effective amount of any one of the foregoing cells or a cell as described herein (such as an, e.g., γδ T cell); a plurality of such cells or a pharmaceutical composition containing such cells in the manufacture of a medicament for the treatment of a solid tumor cell cancer in a subject in need thereof In another aspect, the present invention provides a method of treating cancer in a subject in need thereof, the method comprising administering a therapeutically effective amount of the cells, wherein the cancer comprises solid tumor cells that exhibit cell surface expression of TyrD or GPC3.

In some embodiments, the method comprises simultaneously with the administering of cells or sequentially, administering one or more methods to elevate common gamma chain cytokine(s). In some embodiments, the method comprises performing a plurality of administrations of the cells, wherein the interval between the plurality of administrations is at least about a week, preferably at least about 2, 3, 4, 5, 6, 7, 8, or 12 weeks, and/or no more than once every 6 or 12 months.

In yet another aspect, the present invention provides a pharmaceutical composition for use in any one of the foregoing methods or a method described herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIG. 4 illustrates a manufacturing process for production of engineered γδ CAR-T cells and non-engineered γδ CAR-T cells e.g., for treatment of solid tumors.

FIG. 6 illustrates transduction efficiency of Vδ1 cells with an anti-glypican 3 (GPC3) CAR construct, including soluble IL-15 (sIL 15) (SEQ ID NO:14) and codon optimized (WO 2007/037780A2) sIL15.

DETAILED DESCRIPTION

Definitions

Figure 1:
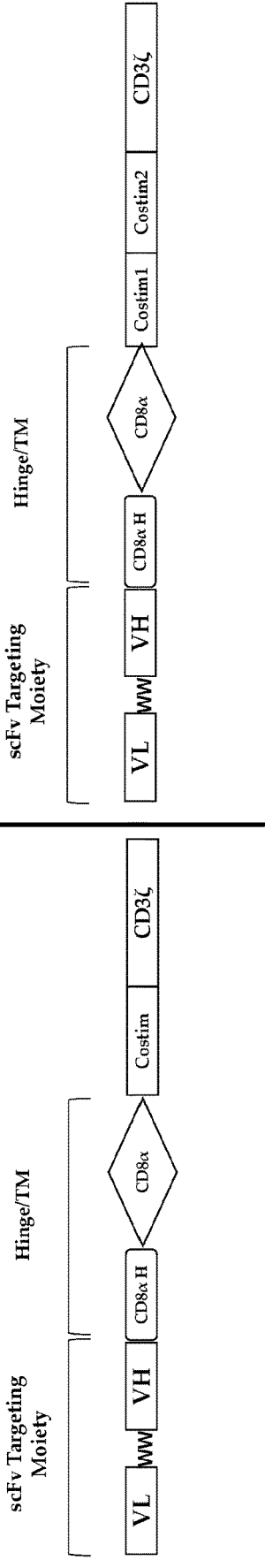
FIG. 1 is a schematic illustration of an embodiment of a chimeric antigen receptor (CAR) containing one costimulatory signaling endodomain (left) or two costimulatory signaling endodomains (right). As used herein costimulatory signaling endodomains are also referred to as costimulation endodomains or costimulatory endodomains. Exemplary costimulatory signaling endodomains useful in exemplary CARs include, without limitation, CD28; CD137 (4-1BB); CD278 (ICOS); CD27; CD134 (OX40); TLR2, and combinations thereof.

For purposes of interpreting this specification, the following definitions will apply, and whenever appropriate, terms used in the singular will also include the plural and vice versa. In the event that any definition set forth conflicts with any document incorporated herein by reference, the definition set forth below shall control. Unless defined otherwise, all technical and scientific terms used herein have the same meaning as commonly understood by one of ordinary skill in the art to which the invention pertains.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "γδ T-cells (gamma delta T-cells)" as used herein refers to a subset of T-cells that express a distinct T-cell receptor (TCR), namely γδTCR, on their surface, composed of one γ-chain and one δ-chain. The term "γδ T-cells" specifically includes all subsets of γδ T-cells, including, without limitation, Vδ1 and Vδ2, Vδ3 γδ T cells, as well as naive, effector memory, central memory, and terminally differentiated γδ T-cells. As a further example, the term "γδ T-cells" includes Vδ4, Vδ5, Vδ7, and Vδ8 γδ T cells, as well as Vγ2, Vγ3, Vγ5, Vγ8, Vγ9, Vγ10, and Vγ11 γδ T cells. In some embodiments, the γδ T-cells are Vδ1$^-$, Vδ2$^-$, or Vδ1$^-$ and Vδ2$^-$. Compositions and methods for making and using engineered and non-engineered γδ T cells and/or sub-types thereof include, without limitation, those described in US 2016/0175358; WO 2017/197347; U.S. Pat. No. 9,499,788; US 2018/0169147; U.S. Pat. No. 9,907,820; US 2018/0125889 and US 2017/0196910, the contents of each of which are incorporated by reference for all purposes, including the said compositions and methods for making and using engineered and non-engineered γδ T cells and/or sub-types thereof. The present application further contemplates T cells, or other engineered leukocytes or lymphocytes, that express one γ-chain or one δ-chain, optionally in combination with a second polypeptide to form a functional TCR. Such engineered leukocytes or lymphocytes, that express one γ-chain or one δ-chain may be used in the methods or present in the compositions described herein.

As used herein, the term "T lymphocyte" or "T cell" refers to an immune cell that expresses or has expressed CD3 (CD3+) and a T Cell Receptor (TCR+). T cells play a central role in cell-mediated immunity. A T cell that "has expressed CD3 and a TCR" has been engineered to eliminate CD3 and/or TCR cell surface expression.

As used herein, the term "TCR" or "T cell receptor" refers to a dimeric heterologous cell surface signaling protein forming an alpha-beta or gamma-delta receptor or combinations thereof. αβTCRs recognize an antigen presented by an MHC molecule, whereas γδTCR can recognize an antigen independently of MHC presentation.

The term "MHC" (major histocompatibility complex) refers to a subset of genes that encodes cell-surface antigen-presenting proteins. In humans, these genes are referred to as human leukocyte antigen (HLA) genes. Herein, the abbreviations MHC or HLA are used interchangeably.

"Activation", as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in antibody molecules in their naturally occurring conformations.

An "antibody light chain," as used herein, refers to the smaller of the two types of polypeptide chains present in antibody molecules in their naturally occurring conformations. κ and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including proteins or peptides, can serve as an antigen. Furthermore, antigens can be derived from recombinant or genomic DNA. A skilled artisan will understand that any DNA that comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full-length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated, synthesized, or can be derived from a biological sample. Such a biological sample can include, but is not limited to a tissue sample, a tumor sample, a cell or a biological fluid.

The term "epitope" includes any protein determinant, lipid or carbohydrate determinant capable of specific binding to an immunoglobulin or T-cell receptor. Epitopic determinants usually consist of active surface groupings of molecules such as amino acids, lipids or sugar side chains and usually have specific three-dimensional structural characteristics, as well as specific charge characteristics. An antibody is said to specifically bind an antigen when the equilibrium dissociation constant ($K_D$) is in a range of $10^{-6}$-$10^{-12}$M.

The term "chimeric antigen receptors (CARs)," as used herein, may refer to artificial T-cell receptors, T-bodies, single-chain immunoreceptors, chimeric T-cell receptors, or chimeric immunoreceptors, for example, and encompass engineered receptors that graft an artificial specificity onto a particular immune effector cell. CARs may be employed to impart the specificity of a monoclonal antibody onto a T cell, thereby allowing a large number of specific T cells to be generated, fur example, for use in adoptive cell therapy. In specific embodiments, CARs direct specificity of the cell to a tumor associated antigen, for example. In some embodiments, CARs comprise an intracellular activation domain (allowing the T cell to activate upon engagement of targeting moiety with target cell, such as a target tumor cell), a transmembrane domain, and an extracellular domain that may vary in length and comprises a disease- or disorder-associated, a tumor-antigen binding region. In particular aspects, CARs comprise fusions of single-chain variable fragments (scFv) derived from monoclonal antibodies, fused to CD3-zeta a transmembrane domain and endodomain. The specificity of other CAR designs may be derived from ligands of receptors (e.g., peptides) or from pattern-recognition receptors, such as Dectins. In certain cases, the spacing of the antigen-recognition domain can be modified to reduce activation-induced cell death. In certain cases, CARs comprise domains for additional co-stimulatory signaling, such as CD3ζ, FcR, CD27, CD28, CD137, DAP 10/12, and/or OX40, ICOS, TLRs (e.g., TLR2), etc. In some cases, molecules can be co-expressed with the CAR, including co-stimulatory molecules, reporter genes for imaging (e.g., for positron emission tomography), gene products that conditionally ablate the T cells upon addition of a pro-drug, homing receptors, chemokines, chemokine receptors, cytokines, and cytokine receptors. Furthermore, one skilled in the art will understand that a costimulatory domain need not be encoded solely by a full-length nucleotide sequence of a gene. It is readily apparent that the present invention includes, but is not limited to, the use of partial nucleotide sequences of more than one gene and that these nucleotide sequences are arranged in various combinations to elicit the desired immune response.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "auto-antigen" means, in accordance with the present invention, any self-antigen which is mistakenly recognized by the immune system as being foreign. Auto-antigens comprise, but are not limited to, cellular proteins, phosphoproteins, cellular surface proteins, cellular lipids, nucleic acids, glycoproteins, including cell surface receptors.

As used herein, the term "autologous" is meant to refer to any material derived from an individual which is later to he re-introduced into the same individual.

As used herein, the term "allogeneic" refers to material derived from an animal which is later introduced into a different animal of the same species.

The term "therapeutically effective amount" refers to the amount of a composition that will elicit a biological or medical response of a tissue, system, or subject that is being sought by the researcher, veterinarian, medical doctor or other clinician. The term "therapeutically effective amount" includes that amount of a composition that, when administered, is sufficient to prevent development of, or alleviate to some extent, one or more of the signs or symptoms of the disorder or disease (e.g., solid tumor) being treated. The therapeutically effective amount will vary depending on the composition, the disease and its severity and the age, weight, etc., of the subject to be treated.

To "treat" a disease as the term is used herein, means to reduce the frequency or severity of at least one sign or symptom of a disease or disorder experienced by a subject.

Administration "in combination with " one or more further therapeutic age includes simultaneous (concurrent) and sequential administration in any order.

The term "pharmaceutically acceptable", as used herein, refers to a material, including but not limited, to a salt, carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The terms "patient," "subject," "individual," and the like are used interchangeably herein, and refer to any animal, amenable to the methods described herein. In certain non-limiting embodiments, the patient, subject or individual is a human.

By the term "specifically hinds," as used herein with respect to an antibody, is meant an antibody which recognizes a specific antigen, but does not substantially recognize or bind other molecules in a sample. For example, an antibody that specifically binds to an antigen from one species may also bind to that antigen. from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

In some embodiments, specific binding can be characterized by an equilibrium dissociation constant of at least about $1 \times 10^{-8}$ M or less (e.g., a smaller $K_D$ denotes a tighter binding). Methods for determining whether two molecules specifically bind are well known in the art and include, for example, equilibrium dialysis, surface plasmon resonance, and the like. Moreover, multi-specific antibodies that bind to a first antigen and one or more additional antigens or a bispecific antibody that binds to two different regions of an antigen are nonetheless considered antibodies that "specifically bind," as used herein.

Solid tumors are tumors that comprise a tumor mass of at least about 10 or at least about 100 tumor cells. The solid tumor can be a soft tissue tumor, a primary solid tumor, or a metastatic lesion.

Examples of solid tumors include, e.g., sarcomas, adenocarcinomas, and carcinomas, of the various organ systems, such as those affecting liver, lung, breast, lymphoid, gastro-intestinal (e.g., colon), genitourinary tract (e.g., renal, urothelial cells), prostate and pharynx. Adenocarcinomas include malignancies such as most colon cancers, rectal cancer, renal-cell carcinoma, liver cancer, non-small cell carcinoma of the lung, cancer of the small intestine and cancer of the esophagus. In one embodiment, the cancer is a melanoma, e.g., an advanced stage melanoma. Metastatic lesions of the aforementioned cancers can also be treated or prevented using the methods and compositions of the invention. Examples of other cancers that can be treated include hone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), primary CNS lymphoma, spinal axis tumor, brain stem glioma, pituitary adenoma, Kaposi's sarcoma, epidermoid cancer, squamous cell cancer, environmentally induced cancers including those induced by asbestos, and combinations of said cancers. In a preferred embodiment, the solid tumor cell expresses, or over-expresses, TyrD, or a fragment thereof. In some embodiments, the solid tumor cell expresses, or over-expresses an HLA: peptide complex containing a TyrD fragment. In some embodiments, the TyrD fragment is $TyrD_{369-377}$. In some embodiments, the HLA is a class I HLA, such as HIA-A2. In some embodiments, the solid tumor cell expresses, or over-expresses $HLA-A2/TyrD_{369-377}$.

In some embodiments, the solid tumor cell expresses, or over-expresses, glypican3 (GPC3). In some embodiments, the solid tumor cell expresses, or over-expresses an epitope of GPC3 that is specifically bound by an anti-GPC3 antibody, T cell Receptor, or chimeric antigen receptor described in U.S. Pat. No. 7,919,086; WO 2014/180306; WO 2018/019772; WO 2016/049459; WO 2003/000883; WO 2006/046751; WO 2007/047291.; WO 2016/08681.3; WO 2016/047722; WO 2016/036973; Cancer Res. 2008;68:9832-9838; Proc Natl Acad Sci U S A. 2013 Mar 19;110(12): E1083-91, the contents of each of which are incorporated by reference in the entirety and for all purposes and in particular for the binding domains, antibodies, antibody fragments, complementarity determining regions, polypeptides containing said complementarity determining regions, nucleic acids encoding for said complementarity determining regions, and epitope specificities and assays for determining epitope specificity described therein. In some embodiments, the solid tumor cell expresses, or over-expresses an epitope of glypican3 that is specifically bound by the anti-GPC3 antibody GC33. In some embodiments, the solid tumor expresses, or over-expresses, an HLA:peptide complex containing a GPC3 fragment. In some embodiments, the HLA is a class I HLA, such as HLA-A2. In some embodiments, the solid tumor expresses, or overexpresses, an HLA:peptide complex containing a GPC3$_{144-152}$ peptide. In some embodiments, the solid tumor expresses, or overexpresses, an HLA:peptide complex containing a GPC3$_{298-306}$ peptide. See, *Oncoimmunology*. 2012 Nov 1; 1(8): 1448-1450.

"Expression cassette" refers to a nucleic, acid comprising expression control sequences operatively linked to a nucleic acid encoding a transcript or polypeptide to be expressed. An expression cassette comprises sufficient cis-acting elements for expression; other elements for expression can he supplied by the host cell or in an in vitro expression system. Expression cassettes can he a component of a vector such as a cosmid, a plasmid (e.g., naked or contained in a liposome), or a virus (e.g., lentivirus, retrovirus, adenovirus, and adeno-associated. virus). An expression cassette can be in a host cell, such as a $\gamma\delta$ T cell.

Ranges: throughout this disclosure, various aspects of the invention can be presented. in a range format It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Chimeric Antigen Receptor Constructs

Aspects of the invention include nucleic acids encoding CARs, and constructs and vectors containing such nucleic acids. In some cases, the nucleic acid is a, e.g., heterologous, component of an expression cassette. In some embodiments, the nucleic acid is a, e.g., heterologous component of a retroviral vector. In some embodiments, the nucleic acid is a, e.g., heterologous, component of an $\alpha\beta$ or $\gamma\delta$ T cell, and preferably a $\gamma\delta$ T cell. In some embodiments, the nucleic acid is a, e.g. heterologous, component of an $\gamma^{30}$ T cell and/or a $\delta^+$T cell. In some embodiments, the nucleic acid is a, e.g., heterologous, component of an $\alpha^-$ T cell and/or a $\beta^-$ T cell.

Described herein are nucleic acids encoding a CAR binding domain that specifically binds to a tumor associated antigen (TAA) expressed on a surface of a solid tumor cell. An exemplary TAA is tyrosinase (TyrD) or a peptide fragment thereof. In some cases, the TAA is glypican3 or a peptide fragment thereof. In some cases, the TAA is a peptide bound to an HLA molecule, such as a class I HLA molecule. Tyrosinase peptides that bind to class I HLA molecules (also referred to herein interchangeably as HLA-restricted tyrosinase epitopes, HLA-restricted tyrosinase epitopes and MHC-restricted tyrosinase antigens) are derived from the tyrosinase enzyme (Genebank Accession No: NP_000363.1) and are typically 8-10 amino acids long, bind to the heavy chain $\alpha1$-$\alpha2$ groove via two or three anchor residues that interact with corresponding binding pockets in the HLA molecule.

Tyrosinase is a membrane-associated N-linked glycoprotein and it is the key enzyme in melanin synthesis. It is expressed in all healthy melanocytes and in nearly all melanoma tumor samples (H. Takeuchi, et al., 2003; S. Reinke, et al., 2005). Peptides derived from this enzyme are presented on MHC class I molecules and are recognized by autologous cytolytic lymphocytes in melanoma patients [T. Wolfel, et al., 1994; Brichard, et al., 1993; Renkvist et al, Cancer immunology immunotherapy 2001 50:3-15; Novellino L, et al., March 2004 update. Cancer lmmunol Immunotherapy. 54;187-207, 2005]. Additional tumor tyrosinase HLA-restricted peptides derived from tumor associated antigens (TAA) can be found at the website of the Istituto Nazionale per to Studio e la Cura dei Tumori at www.istitutotumori.mi.it.

Non-limiting examples of MHC class I restricted tyrosinase antigenic peptides are provided in WO2008/120202, which is fully incorporated herein by reference in its entirety, e.g., in Table 139 of WO2008/120202. According to some embodiments of the invention, the tyrosinase antigenic peptide is the TyrD$_{369-377}$ peptide. Binding domains that specifically bind. TyrD, an epitope within TyrD, including but not limited to those that bind in an HLA (e.g., class 1 HLA) restricted manner, include without limitation those described in WO 2016/199140; WO 2016/199141; U.S. Pat. No. 9,688,739; and in co-pending application PCT/IB2017/053539, the contents of each of which are incorporated by reference in the entirety and for all purposes including but not limited to compositions and methods for identifying, making, and using binding domains that specifically bind TyrD, or an epitope within TyrD, e.g., in an HLA-restricted or HLA-independent manner.

GPC3 peptides that bind to class I HLA molecules (also referred to herein interchangeably as HLA-restricted GPC3 epitopes, HLA-restricted GPC3 epitopes and MHC-restricted GPC3 antigens) are derived from the glypican3 protein (Genebank Accession No: NM_001164617.2) and are typically 8-10 amino acids long, bind to the heavy chain $\alpha1$-$\alpha2$ groove via two or three anchor residues that interact with corresponding binding pockets in the HLA molecule.

As used herein, a binding domain, CAR, or CAR T cell, that specifically binds TyrD and/or specifically hinds an epitope within TyrD includes, without limitation, binding domains, CARs, or CAR T cells that specifically bind a TyrD peptide fragment. The binding domains, CARs, or CAR T cells that specifically bind a TyrD peptide fragment can specifically bind the referenced TyrD peptide fragment in an HLA-restricted manner. Similarly, as used herein, a cell that expresses TyrD on the surface of the cell includes cells that express, or over-express, a TyrD peptide fragment on the surface of the cell, such as in a peptide:HLA complex.

As used herein, a binding domain, CAR, or CAR T cell, that specifically binds GPC3 and/or specifically binds an epitope within GPC3 includes, without limitation, binding domains, CARs, or CAR T cells that specifically bind a GPC3 peptide fragment. The binding domains, CARs, or CAR T cells that specifically bind a GPC3 peptide fragment can specifically bind the referenced GPC3 peptide fragment in an HLA-restricted manner. Similarly, as used herein, a cell that expresses TyrD on the surface of the cell includes cells that express, or over-express, a GPC3 peptide fragment on the surface of the cell, such as in a peptide:HLA complex.

In some embodiments, the binding domain binds the antigen as expressed in a full-length functional polypeptide on the surface of a cell. In some embodiments, the binding domain binds the antigen as presented in an MHC:antigen complex. In some embodiments, the binding domain binds the antigen in an HLA-restricted manner. Binding domains exhibiting specificity for MHC:antigen complexes are described, e.g., in WO/2016/199140 and WO/2016/199141.

In some embodiments, the isolated nucleic acid encodes an anti-TyrD binding domain having a CDRH1 comprising TSGMGVS (SEQ ID NO: 33), a CDRH2 comprising HIYWDDDKRYNPSLKS (SEQ ID NO: 34), a CDRH3 comprising KDYGSSFYAMHY (SEQ ID NO: 35), CDRL1 comprising (SEQ ID NO: 36), a CDRL1 comprising YTSTLQP (SEQ ID NO: 37), and/or a CDRL2 comprising LQYDNLWT (SEQ ID NO: 38).

In some embodiments, the isolated nucleic acid encodes an anti-GPC3 binding domain having a CDRH1 comprising DYEMH (SEQ ID NO: 39) (or GYTFTDYEMH (SEQ ID NO: 40)), a CDRH2 comprising ALDPKTGDTAY-SQKFKG (SEQ ID NO: 41), a CDRH3 comprising FYSYTY (SEQ ID NO: 42), CDRL1 comprising RSSQSLVHSNRNTYLH (SEQ ID NO: 43), a CDRL2 comprising KVSNRFS (SEQ ID NO: 44), and/or a CDRL3 comprising SQNTHVPPT (SEQ ID NO: 45).

The present disclosure also contemplates anti-TyrD or anti-GPC3 binding domains that compete for binding with a sequence provided herein. One can determine whether an anti-TyrD binding domain binds to the same epitope as, or competes for binding with, a reference antibody or binding domain by using known methods. For example, to determine if a test antibody binds to the same epitope as a reference binding domain, the reference binding domain can be allowed to bind to TyrD under saturating conditions. Next, the ability of a test binding domain to bind to TyrD molecule can be assessed. If the test binding domain is able to bind to TyrD following saturation binding with the reference binding domain, it can be concluded that the test binding domain binds to a different epitope than the reference binding domain. On the other hand, if the test binding domain is not able to bind to TyrD following saturation binding with the reference binding domain, then the test binding domain may bind to the same epitope as the epitope bound by the reference binding domain.

To determine if a binding domain competes for binding with a reference binding domain, the above-described binding methodology is performed in two orientations: In a first orientation, the reference binding domain is allowed to bind to TyrD under saturating conditions followed by assessment of binding of the test binding domain to the TyrD molecule. In a second orientation, the test binding domain is allowed to bind to a TyrD molecule under saturating conditions followed by assessment of binding of the reference binding domain to the TyrD molecule. If, in both orientations, only the first (saturating) binding domain is capable of binding to the TyrD molecule, then it is concluded that the test binding domain and the reference binding domain compete for binding to TyrD. As will be appreciated by a person of ordinary skill in the art, a binding domain that competes for binding with a reference binding domain may not necessarily bind to the identical epitope as the reference binding domain, but may sterically block binding of the reference binding domain by binding an overlapping or adjacent epitope. The methods described above to determine competition and epitope binding with an anti-TyrD binding domain can likewise be applied to an anti-TyrD binding domains.

Two binding domains bind to the same or overlapping epitope if each competitively inhibits (blocks) binding of the other to the antigen. That is, a 1-, 5-, 10-, 20- or 100-fold excess of one binding domain inhibits binding of the other by at least 50%, for example, 75%, 90% or even 99% as measured in a competitive binding assay (see, e.g., Junghans et al., Cancer Res. 1990 50:1495-1502). Alternatively, two binding domains have the same epitope if essentially all amino acid mutations in the antigen that reduce or eliminate binding of one binding domain reduce or eliminate binding of the other. Two binding domains have overlapping epitopes if some amino acid mutations that reduce or eliminate binding of one binding domain reduce or eliminate binding of the other.

Additional routine experimentation (e.g., peptide mutation and binding analyses) can then be carried out to confirm whether the observed lack of binding of the test binding domain is in fact due to binding to the same epitope as the reference binding domain or if steric blocking (or another phenomenon) is responsible for the lack of observed binding. Experiments of this sort can be performed using ELISA, RIA, surface plasmon resonance, flow cytometry or any other quantitative or qualitative binding assay available in the art.

The present disclosure provides antibodies and CARs with "substantial identity" or "substantial similarity" to the sequences provided herein in the CDR or framework regions. The term "substantial identity" or "substantially identical," when referring to a nucleic acid or fragment thereof, indicates that, when optimally aligned with another nucleic acid (or the complementary strand of the other nucleic acid), there is nucleotide sequence identity in % for example, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% sequence identity. In some aspects, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine tyrosine, and tryptophan; 5) basic side chains: lysine,-arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix.

Sequence identity and/or similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Sequences also can be compared using the Smith-Waterman homology search algorithm using an affine gap search with a gap open penalty of 12 and a gap extension penalty of 2, BLOSUM matrix of 62. Another preferred algorithm when comparing a sequence disclosed herein to a database containing a large number of sequences from different organisms is the computer program BLAST, especially BLASTP or TRLASTN, using default parameters. See, e.g., Altschul et al. (1990) J. Mol. Biol. 215: 403-410 and (1997) Nucleic Acids Res. 25:3389-3402, each of which is herein incorporated by reference.

Provided herein are anti-TyrD or anti-GPC3 CARs comprising variants of any of the HCVR, LCVR, and/or CDR amino acid sequences disclosed herein having one or more substitutions (e.g., conservative substitutions). For example, the present disclosure includes anti-TyrD CARs having HCVR, LCVR, and/or CDR amino acid sequences with, e.g., 20 or fewer, 19 or fewer, 18 or fewer, 17 or fewer, 16 or fewer, 15 or fewer, 14 or fewer, 13 or fewer, 1.2 or fewer, 11 or fewer, 10 or fewer, 9 or fewer, 8 or fewer, 7 or fewer, 6 or fewer. 5 or fewer, 4 or fewer, 3 or fewer, 2 or fewer, or 1 amino acid substitutions relative to any of the 14CVR, LCVR, and/or CDR (e.g., HCDR1, HCDR2, HCDR3, LCDR1, LCDR2, or LCDR3) amino acid sequences disclosed herein. For example, an anti-TyrD CAR can comprise 20, 19, 18, 17, 16, 15, 14 13, 12, 11, 10, 9, 8, 7, 6, 5, 4, 3, 2, or 1 amino acid substitutions (e.g., conservative amino acid substitutions) relative to any of the HCVR LCVR, and/or CDR (e.g., HCDR1, HCDR2, HCDR3, LCDR1, LCDR2, or LCDR3) amino acid sequences disclosed herein.

Similarly, the present disclosure includes anti-GPC3 CARs having HCVR, LCVR, and/or CDR amino acid sequences with, e.g., 20 or fewer, 19 or fewer, 18 or fewer, 17 or fewer, 16 or fewer, 15 or fewer, 14 or fewer, 13 or fewer, 12 or fewer, 11 or fewer, 1.0 or fewer, 9 or fewer, 8 or fewer, 7 or fewer, 6 or fewer, 5 or fewer, 4 or fewer, 3 or fewer, 2 or fewer, or 1 amino acid substitutions relative to any of the HCVR, LCVR, and/or CDR (e.g., HCDR1, HCDR2, HCDR3, LCDR1, LCDR2, or LCDR3) amino acid sequences disclosed herein. For example, an anti-GPC3 CAR can comprise 20, 19, 18, 17, 16, 15, 14 13, 12, 11, 10, 9, 8, 7, 6, 5, 4, 3, 2, or 1 amino acid substitutions (e.g., conservative amino acid substitutions) relative to any of the HCVR, LCVR, and/or CDR (e.g., HCDR1, HCDR2, HCDR3, LCDR1, LCDR2, or LCDR3) amino acid sequences disclosed herein.

Exemplary binding domains described herein typically comprise, in order from the amino to carboxy terminus, a heavy chain region followed by a light chain region (VH-VL). Where a certain order of of VH and VL region in the binding domain is explicitly or implicitly described, the present disclosure is also understand to describe the alternate embodiment in which the order of VH and VL regions are reversed, e.g., in an scFV or a CAR comprising an scFv binding domain. Thus, description of a VH-VL order also describes the alternate VL-VH order, e.g., in an scFV or a CAR comprising an scFv binding domain. Moreover, description of a VL-VH order also describes the alternate VH-VL order, e.g., in an scFV or a CAR comprising an scFv binding domain.

Generally, the CAR encoding nucleic acids described herein include an extracellular linker portion that encodes a peptide linker that links the binding domain to a transmembrane domain. Exemplary linker portions include, without limitation, a linker portion that encodes the CD8α hinge domain, e.g., SEQ ID NO:1 (PTPAPTIASQPLSLRPEACR-PAAGGAVHTRGLDFACDIY) or SEQ ID NO:2 (TTTPA-PRP PTPAPTIASQPLSLRPEACRPAAGGAVHTRGLD-FACDIY). Typically, the region encoding the peptide linker (e.g., CD8α hinge domain) is 3' of the region encoding the binding domain and 5' of a region encoding a transmembrane domain.

The CAR encoding nucleic acids described herein include a transmembrane domain. The transmembrane domain can link an extracellular antigen binding domain, e.g., and hinge, to one or more intracellular signaling components. For example, the transmembrane domain can link an antigen binding domain, e.g., and hinge, to a CD3ζ signaling domain and optionally with one or two costimulation endodomains. Exemplary transmembrane domains include without limitation a CD8α transmem branc domain, SEQ ID NO:3 (IWAPLAGTCGVLLLSLVITLYC). Typically, the region encoding the transmembrane domain (e.g., CD8α transmenrbrane-domain) is 3'of the region encoding the peptide linker (e.g., CD8α hinge domain) and 5' of a region encoding one or more cytoplasmic domains.

In some embodiments, the isolated nucleic acid encodes a cytoplasmic region containing one or more cytoplasmic domains. The region encoding the cytoplasmic region is typically 3' of the region encoding the transmembrane domain. The cytoplasmic domains are typically signaling domains that provide an activating signal for γδ T cell proliferation, cytotoxic activity, and/or pro-inflammatory cytokine expression (e.g., TNF-α or IFNγ). An exemplary cytoplasmic domain is a CD3ζ signaling domain. In some embodiments, the CD3ζ signaling domain is or comprises SEQ ID NO:4 (RVKFSRSADAPAYQQGQNQLY-NELNLGR REEYDVLDKRR-GRDPEMGGKPQRRKNPQEGLYNELQKDKMAEAY-SEIGMKGERRRGK GHDGLYQGLSTATKDTYDALHMQALPPR). In some embodiments, the CD3ζ signaling domain is or comprises SEQ ID NO:5 (RVKFSRSADAPAYQQGQNQLYNELNL-GRREEYDV LDKRRGRDPEMGGKPRRKNPQEGLY-NELQKDKMAEAYSEIGMKGERRGKGHDGLY QGL-STATKDTYDALHMQALPPR). In some embodiments, the cytoplasmic region contains multiple (e.g., 2, 3, 4, 5, or 6) signaling domains, such as multiple (e.g., 2, 3, 4, 5, or 6) CD3ζ signaling domains, e.g., each independently selected from SEQ ID NO: 4 and 5. In some embodiments, the cytoplasmic region contains multiple (e.g., 2, 3, 4, 5, or 6) non-CD3ζ signaling domains and a CD3ζ signaling domain. In some embodiments, the cytoplasmic region contains a non-CD3ζ signaling domain and multiple (e.g., 2, 3, 4, 5, or 6) CD3ζ signaling domains. Additional or alternative signaling domains include, without limitation.

The cytoplasmic region can contain one or more costimulation endodomains. A region encoding one or more costimulation endodomains can be 5' or 3' of a region encoding a signaling domain, In some embodiments, the region encoding one or more costimulation endodomains is 5' of the region encoding a signaling domain. In some embodiments, a region encoding one or more costimulation endodomains is 5' of a signaling domain and an additional region encoding one or more costimulation endodomains is 3' of the signaling domain. Exemplary costimulation endodomains include, without limitation, CD28; CD137 (4-1BB); CD278 (ICOS); CD27; CD134 (OX40); and TLR2 costimulation endodomains, and combinations thereof.

In some embodiments, additional signaling modalities can be included to increase proliferation, persistence, and/or cytotoxic activity of the γδ-T cells described herein. For example, in some embodiments, the CAR construct can encode a soluble common gamma chain cytokine at the 3' end of the isolated nucleic acid. The common gamma chain cytokine encoding region can be linked to the 5' portion of the CAR onstruct via a T2A linker encoding-region, such that the common gamma chain cytokine is cleaved from the CAR polypeptide and secreted by the cell.

In some embodiments, the construct encodes at least one 4-1BB costimulation endodomain, and optionally a second costimulation endodomain selected from a 4-1BB, ICOS, CD28, and CD27 costimulation endodomain. In some embodiments, the construct encodes at least two 4-1BB costimulation endodomains, or two 4-1BB costimulation endodomains in combination with one, two, three, or four, or more, costimulation endodomains selected from a 4-1BB, LCOS, CD28, and CD27. In some embodiments, the 4-1BB costimulation endodomain comprises SEQ ID NO: 6 (KR-GRKKLLYIFKQPFMRPVQTT QEEDGCSCRFPEEEEGGCEL).

In some embodiments, the construct encodes one CD27 costimulation endodomain, and optionally a second costimulation endodomain selected from a 4-1BB, ICOS, CD28, and CD27 costimulation endodomain. In some embodiments, the construct encodes a CO27 costimulation endodomain, and a 4-1BB costimulation endodomain. In some embodiments, the construct encodes two CD27 costimulation endodomains. in some embodiments, the CO27 costimulation endodomain comprises SEQ ID NO: 7 (QRRKYRSNKGESPVEPAEPCITYSCPREEEGSTIP-IQED YRKPEPACSP).

In some embodiments, the construct encodes a secretion signal, e.g., SEQ ID NO: 12 (MALPVTALLLPLAELL-HAARP) operably linked to facilitate secretion of a C-terminal polypeptide, such as a cytokine that supports the activation, cytotoxicity, and/or persistence of a T cell (e.g., CAR-T cell). In some embodiments, the secretion signal is a secretion signal of SEQ ID NO: 26 (MRISKPHIRSI-SIQCYLCLUNSHELTEAGIFIVEILGCFSAGLPKTEA). In some embodiments, the construct encodes a secretion signal, e.g., SEQ ID NO: 12 operably linked to facilitate secretion of a common gamma chain cytokine such as IL-15 or an active fragment thereof, e.g., SEQ ID NO: 14 (NWVN-VISDLKKIEDLIQSMIHDATLYT ESDVHP-SCKVTAMKCFLLELQVISLESG-DASIHDTVENLHLANNSLSSNGNVTESGCKEC EELEEKNIKEFLQSFVIIIVQMFINTS). Other IL-15 sequences, including codon optimized nucleic acid sequences encoding sIL15, are disclosed in WO 2007/037780. Exemplary common gamma chain cytokines include IL-2 and IL-15. In some embodiments, the common gamma chain cytokine is selected from IL-2, IL-7, and IL-15

In some embodiments, the construct encodes one or more multi-cistronic linker regions, e.g., between a signaling domain and/or costimulation endodomain and a secretion signal operably linked to facilitate secretion of a cytokine. A multi-cistronic linker region is a region of polypeptide sequence or RNA sequence that facilitates the production of multiple discrete polypeptides from a single transcription product. In some embodiments, the multi-cistronic linker region encodes a cleavage sequence. Suitable cleavage sequences include self-cleavage sequences such as a P2A, F2A, E2A, or T2A cleavage sequence and/or sequences that are cleaved by an endogenous protease, such as furin.

In some embodiments, the cleavage sequence is a P2A cleavage sequence. In some embodiments, the cleavage sequence is a furin cleavage sequence. In some embodiments, the cleavage sequences are a P2A and a furin cleavage sequence. In some embodiments, the cleavage sequence is the P2A cleavage sequence of SEQ ID NO: 15 (SGSGATNFSLLKQAGDVEENPGP). In some embodiments, the cleavage sequence is a furin cleavage sequence of SEQ ID NO: 16 (RAKR). In some embodiments, the cleavage sequence is a P2A+furin cleavage sequence of SEQ ID NO: 17 (RAKRSGSGATNFSLLKQAGDVEENP GP). In some embodiments, the cleavage sequence is the P2A cleavage sequence of SEQ ID NO: 25 (GSGATNFSLLKQAGD-VEENPGP).

In some embodiments, the cleavage sequence is or comprises a P2A cleavage sequence of SEQ ID NO: 27 (ATNFSLLKQAGDVEENPGP). In some embodiments, the cleavage sequence is or comprises an F2A cleavage sequence of SEQ ID NO: 28 (VKQTLNNFDLLKLAGD-VESNPGP). In some embodiments, the cleavage sequence is or comprises an E2A cleavage sequence of SEQ ID NO: 29 (QCTNYALLKLAGDVESNPGP). In some embodiments, the cleavage sequence is or comprises an T2A cleavage sequence of SEQ ID NO: 30 (EGRSLLTCGD-VEENPGP). In certain aspects, multiple self-cleavage sequences can be encoded carboxy terminal to a signaling and/or costimulatory domain and amino-terminal to an encoded secreted cytokine (e.g., common gamma chain cytokine such as IL-15), preferably wherein the multiple self cleavage sequences are independently selected from the group consisting of a P2A cleavage sequence, a T2A cleavage sequence, an E2A cleavage sequence, and an F2A cleavage sequence. In certain aspects, one or more self-cleavage sequences and one or more sequences cleaved by an endogenous protease are encoded in a construct described herein. In certain embodiments, a endogenous protease recognition site is encoded amino terminal to a self cleavage sequence.

In some embodiments, the multi-cistronic linker region encodes an internal ribosome entry site. An exemplary internal ribosome entry site is encoded by SEQ ID NO: 31 (CTAACGTTACTGGCCGAAGCCGCTTG-GAATAAGGCCGGTGTGGGTTTGTCTATATGT TAT-TTTCCACCATATTGCCGTCTTTTGGCAATGT-GAGGGCCCGGAAACCTGGCCCTGT CTTCTTGACGAGCAT-TCCTAGGGGTCTTTCCCCTCTCGC-CAAAGGAATGCAAGGTCT GTTGAATGTCGT-GAAGGAAGCAGTTCCTCTGGAAGC TTCTTGAAGACAAACAACGTC TGTAGCGACCCTTTGCAGGCAGCGGAACCCCC-CACCTGGCGACAGGTGCCTCTGCG GCCAAAAGC-CACGTGTATAAGATA-CACCTGCAAAGGCGGCACAACCCCAGTGCCAC GTTGTGAGTTGGATAGTTGTGGAAAGAGT-CAAATGGCTCTCCTCAAGCGTATTCAAC AAGGGGCTGAAGGATGCCCAGAAGGTACCCCAT-TGTATGGGATCTGATCTGGGGCC TCGGTGCA-CATGCTTTACATGTGTTTAGTCGAGGT-TAAAAAAACGTCTAGGCCCCCC GAACCACGGGGACGTGGTTTTCCTTT-GAAAAACACGATGATA).

Another exemplary internal ribosome entry site is encoded by SEQ ID NO: 32 (AGCAGGTTTCCC-CAACTGACACAAAACGTGCAACTT-GAAACTCCGCCTGGTCTTTC CAGGTCTAGAGGGGTAACACTTTGTAC TGCGTTTGGCTCCACGCTCGATCCACTGGC GAGTGTTAGTAACAGCACTGTTGCTTCGTAGCG-GAGCATGACGGCCGTGGGAACTCC TCCTTGGTAACAAGGACCCACCCACGGGGC-CAAAAGCCACGCCCACACGGGCCCGTCATG TGTGCAACCCCAGCACGGCGACTT-TACTGCGAAACCCACTTTAAAGTGACATTGAAA CTGGTACCCACACACTGGTGACAGGCTAAGGAT GCCCTTCAGGTACCCCGAGGTAA CACGCGACACTCGGGATCT-GAGAAGGGGACTGGGGCTTC-TATAAAAGCGCTCGGTT TAAAAAGCTTCTATGCCT-GAATAGGTGACCGGAGGTCGGCA CCTTTCCTTTGCAATT ACTGACCAC).

Further suitable internal ribosome entry sites include, but are not limited to, those described in Nucleic Acids Res. 2010 Jan;38(Database issue):D131-6. doi: 10.1093/nar/gkp981. Epub 2009 Nov 16, those described at iresite.org, those described in WO 2018/215787, the sequence described in GenBank accession No. KP019382.1, and the IRES element disclosed in GenBank accession No. LT727339.1, the contents of which are incorporated by reference in the entirety and for all purposes and in particular for the internal ribosome entry sites and their use described therein.

Additional multi-cistronic linker regions, including cleavage self-cleavage, and IRES elements, are disclosed in US 2018/0360992 and U.S. Pat. No. 8,865,467.

In some embodiments, the isolated nucleic acid encodes SEQ ID NO:8 (MSVPTQVLGLLLLWLT-DARCDIQMTQSPSSLSASVGDRVTITCKASQ-DIHNYIAWYQQ KPGKAPKLLIHYT-STLQPGVPSRFSGSGSGTDFTFTISSLQPED IATYYCLQYDNLWTFGQ GTKVEIKRGGGGSGGGGSGGGGQI TLKESGPTLVKPTQTLTLTCTFSGFSLSTSGMGVS WIRQPPGKALEWLA-HIYWDDDKRYNPSLKSRLTITKDTSK NQVVLTMTNMDPVDTATY YCARKDYGSSFYAM-HYWGQGTLVTVSSTTTPAPRPPTPAPTIA-SQPLSLRPEACRPAAG GAVHTRGLDFACDIYI-WAPLAGTCGVLLISLVITLYCKRGRKK LLYIFKQPFMRPVQTT QEEDGCSCRFPEEEEGGCELRVKFSRSADAPA-YQQGQNQLYNELNLGRREEYDVLDKR RGRDPEMGGKPQRRKNPQEGLYNELQKDKMAEAY-SEIGMKGERRRGKGHDGLYQGLS TATKDTY-DALHMQALPPR), a hD11-CD8-BBz polypeptide comprising an hD11 anti-TyrD binding domain (anti-TyrD$_{369\text{-}377}$), a CD8α hinge and transmembrane region, a 4-1BB costimulation endodomain, and a CD3ζ signaling domain.

In some embodiments, the isolated nucleic acid encoding an anti-TyrD$_{369\text{-}377}$-CD8-BBz polypeptide comprises the sequence of SI Q ID NO:9 (ATGTCCGTGCC-TACCCAGGTGCTGGGCCTGCTGCTGCTG TGGCTGACCGACGCCAG ATGCGACATCCA-GATGACCCAGTCTCCATCCTCCCTGTCTG-CATCTGTAGGAGACAG AGTCACCAT-CACTTGCAAGGCGAGTCA GGACATTCACAACTATATAGCTTGGTATCA GCAGAAACCAGGGAAAGCCCCTAAGCTCCTGATC-CACTATACATCCACTTTCAACC AGGGGTCCCAT-CAAGGTTCAGTGGAAGTGGATCTGGGACAGATTT-TACTTTCACCAT CAGCAGCCTGCAGCCTGAAGATATTGCAACATAT-TACTGTCTACAGTATGATAATCT CTGGACGTTCGGT-CAAGGCACCAAGGTGGAAATCAAACGGGGTG-GAGGTGGATCTG GAGGAGGAGGATCCGGTGGAGGAGGTCAGAT-CACCTTGAAGGAGTCTGGTCCTACG CTGGT-GAAACCCACACAGACCCT-CACGCTGACCTGCACCTTCTCTGGGTTCTCACTC AGCACTAGTGGAATGGGTGTGTCCTG-GATCCGTCAGCCCCCAGGAAAGGCCCTGGA GTGGCTTGCACACATTTATTGGGATGATGA-TAAGCGCTACAACCCATCTCTGAAGAG CAGGCT-CACCATCACCAAGGACACCTC-CAAAAACCAGGTGGTCCTTACAATGACCA ACATGGACCCTGTGGACACAGCCACATAT-TACTGTGCACGAAAGGACTACGGTAGT AGCTTC-TATGCTATGCACTACTGGGGTCAAGGAACCCTAGT-CACCGTGTCGAGTACC ACGACGCCAGCGCCGCGACCAC-CAACACCGGCGCCCACCATCGCGTCGCAGCCCCT GTCCCTGCGCCCAGAGGCGTGCC GGCCAGCGGCGGGGGGCGCAGTGCACACCAGGG GGCTGGACTTCGCCTGTGATATCTA-CATCTGGGCFCCCTTGGCCGGGACTTGTGGGG TCCTTCTCCTGTCACTGGTTATCACCCTT-TACTGCAAACGGGGCAGAAAGAAACTCC TGTATATATTCAAACAACCATTTATGAGACCAGTA-CAAACTACTCAAGAGGAAGAT GGCTGTAGCTGCC-GATTTCCAGAAGAAGAAGAAGGAGGATGTGAACT-GAGAGTGAA GTTCAGCAGGAGCGCA- GACGCCCCCGCGTACCAGCAGGGC
CAGAACCAGCTCTATA ACGAGCT-
CAATCTAGGACGAAGAGAGGAGTAC-
GATGTTTTGGACAAGAGACGTGGC CGGGACCCT-
GAGATGGGGGGGAAAGCCGCAGAGAAG
GAAGAACCCTCAGGAAGGCC TGTACAAT-
GAACTGCAGAAAGATAAGATGGCCGAGGCCTA-
CAGTGAGATTGGGATG AAAGGCGAGCGCCG-
GAGGGGCAAGGGGCACGATGGCCTTTA
CCAGGGTCTCAGTAC AGCCACCAAGGACACC-
TACGACGCCCTTCA-
CATGCAGGCCCTGCCCCCTCGCTAA).

In some embodiments, the isolated nucleic acid comprises a codon optimized sequence encoding a CD8α hinge region. Exemplary codon optimized CD8α hinge region nucleic acid sequences include, without limitation, SEQ ID NO: 10 (ACCACCACCCCTGCAC-
CAAGGCCCCCGACTCCCGCGCCCACCATCGCGT-
CACA GCCTCTTAGCCTGCGACCGGAAGCATGCA-
GACCAGCTGCCGGGGGGGCCGTGCATA
CGAGAGGTTTGGACTTCGCCTGCGAT). In some embodiments, the CD8α hinge region is encoded by the following sequence SEQ ID No: 11 (AC-
CACGACGCCAGCG CCGCGACCAC-
CAACACCGGCGCCCAC-
CATCGCGTCGCAGCCCCTGTCCCTGCGCCCA
GAGGCGTGCCGGCCAGCGGCGGGGGG
CGCAGTGCACACGAGGGGGCTGGACTTCG CCTGT-
GAT).

In some embodiments, the isolated nucleic acid encodes SEQ ID NO: 18 (MSVPTQVLGLLLLWLT-
DARCDIQMTQSPSSLSASVGDRVTATCKASQ-
DIHNYIAQYQQ KPGKAPKLLIHYT-
STLQPGVPSRFSGSGSGTDFTFTISSL
QPEDIATYYCLQYDNLQTFGQ
GTKVEIKRGGGGSGGGGSGGGGQITL-
KESGPTLVKPTQTLTLTCTGSGFSLSTSGMGVS
WIRQPPGKALEWLA-
HIYWDDDKRYNPSLKSRLTITKD
TSKNQVVLTMTNMDPVDTATY YCARKDYGSSFY-
AMHYWGQGTLVTVSSTTTPAPRPPTPAPTIA-
SQPLSLRPEACRPAAG GAVHTRGLDFACDIYI-
WAPLAGTCGVLLLSLVITLYCKRGRK
KLLYIFKQPFMRPVQTT
QEEDGCSCRFPEEEEGGCELRVKFSRSADAPA-
YQQGQNQLYNELNLGRREEYDVLDKR
RGRDPEMGGKPQRRKNPQEGLYNELQKDKMAEAY-
SEIGMKGERRRGKGHDGLYQGLS TATKDTY-
DALHMQALPPRRAKRSGSGATNFSLLKQAGDVEEN-
PGPMALPVTALLPLA
LLLHAARPMWVNVISDLKKIEDLIQSMHIDAT-
LYTESDVHPSCKVTAMKCFLLELQVISL ESG-
DASIHDTVENLHLANNSLSSNGNVTESGCKE-
CEELEEKNIKEFLQSFVHIVQMFINTS *), a hD11-CD8-BBz-sIL15 polypeptide comprising an anti-TyrD hD11 (anti-TyrD$_{369-377}$) binding domain, a CD8α hinge and transmembrane region, a 4-1BB costimulation endodomain, a CD3ζ signaling domain, a furin-P2A cleavage sequence, and a secretiOn signal operably linked to an IL-15 domain.

In some embodiments, the isolated nucleic acid encoding at hD11-CD8-BBz-sIL15 polypeptide comprises the sequence of SEQ ID NO: 19 (ATGTCCGTGCCTACCCAG
GTGCTGGGCCTGCTGCTGCTGTGG
CTGACCGACGCCAGATGCGACATCCAGATGACC
CAGTCTCCATCCTCCCTGTCTGCATCTGTAGGA-
GACAGAGTCACCATCACTTGCAAG
GCGAGTCAGGACATTCACAAC- TATATAGCTTGGTATCAGCAGAAACCAGGGAAAGC
CCCTAAGCTCCTGATCCACTATACATC-
CACTTTGCAACCAGGGGTCCCATCAAGGTT
CAGTGGAAGTGGATCTGGGACAGATTTTACTTT-
CACCATCAGCAGCCTGCAGCCTGA AGATATTGCAA-
CATATTACTGTCTACAGTATGA-
TAATCTCTGGACGTTCGGTCAAGG
CACCAAGGTGGAAATCAAACGGGGTGGAGGTG-
GATCTGGAGGAGGAGGATCCGGT GGAG-
GAGGTCAGATCACCTTGAAGGAGTCTGGTCC-
TACGCTGGTGAAACCCACACA
GACCCTCACGCTGACCTGCACCTTCTCTGGGTTCT-
CACTCAGCACTAGTGGAATGGG TGTGTCCTG-
GATCCGTCAGCCCCCAGGAAAGGCCCTG-
GAGTGGCTTGCACACATTTA
TTGGGATGATGATAAGCGCTACAACCCATCTCT-
GAAGAGCAGGCTCACCATCACCA AGGACACCTC-
CAAAAACCAGGTGGTCCTTACAATGACCAA-
CATGGACCCTGTGGAC
ACAGCCACATATTACTGTGCACGAAAGGAC-
TACGGTAGTAGCTTCTATGCTATGCAC TACTGGGGT-
CAAGGAACCCTAGTCACCGTGTCGAGTACCAC-
CACCCCTGCACCAAG
GCCCCCCGACTCCCGCGCCCACCATCGCGT-
CACAGCCTCTTAGCCTGCGACCGGAAGC ATGCA-
GACCAGCTGCCGGGGGGGCCGTGCAT-
ACGAGAGGTTTGGACTTCGCCTGCG
ATATCTACATCTGGGCGCCCTTGGCCGGGACTTGT
GGGGTCCTTCTCCTGTCACTGGT TATCACCCTT-
TACTGCAAACGGGGCAGAAAGAAACTCCTGTATAT-
ATTCAAACAACC ATTTATGAGACCAGTACAAAC-
TACTCAAGAGGAAGATGGCTGTAGCTGCCGATTTCC
AGAAGAAGAAGAAGGAGGATGTGAACTGAGAGT-
GAAGTTCAGCAGGAGCGCAGAC
GCCCCCGCGTACCAGCAGGGCCAGAACCAGCTC-
TATAACGAGCTCAATCTAGGACG AAGAGAG-
GAGTACGATGTTTTGGACAAGA-
GACGTGGCCGGGACCCTGAGATGGGGG
GAAAGCCGCAGAGAAGGAAGAACCCTCAG-
GAAGGCCTGTACAATGAACTGCAGAA AGATAA-
GATGGCGGAGGCCTACAGTGAGATTGGGAT-
GAAAGGCGAGCGCCGGAGG
GGCAAGGGGCACGATGGCCTT-
TACCAGGGTCTCAGTACAGCCACCAAGGACACCTA
CGACGCCCTTCA-
CATGCAGGCCCTGCCCCCTCGCCGCGCGAAGC-
GATCAGGCAGCG GGGCGACAAATTTCAGCCTTCT-
GAAACAAGCAGGCGACGTGGAAGAAAACCCCGGT
CCAATGGCCT-
TACCAGTGACCGCCTTGCTCCTGCCGC
TGGCCTTGCTGCTCCACGCC
GCCAGGCCGAACTGGGTGAATGTAATAAGTGATTT-
GAAAAAAAATTGAAGATCTTAT TCAATCTATGCATAT-
TGATGCTACTTATATACGGAAAGTGATGTT-
CACCCCAGTTTGC
AAAGTAACAGCAATGAAGTGCTTTCTCTTGGAGT-
TACAAGTTATTTCACTTGAGTCC GGAGATGCAAGT-
ATTCATGATACAGTAGAAAATCTGAT-
CATCCTAGCAAACAACAG
TTTGTCTTCTAATGGGAATGTAACAGAATCTG-
GATGCAAAGAATGTGAGGAACTGG
AGGAAAAAAATATTAAAGAAT-
TTTTGCAGAGTTTTGTACATATTGTCCAAATGTTCA
TCAACACTTCTTGA).

In some embodiments, the isolated nucleic acid encodes SEQ ID NO: 20 (MSVPTQVLGLLLLWLT-
DARCQVQLVQSGAEVKKPGASVKVSCK- ASGYTFTDYEMHW VRQAPGQ-
GLEWMGALDPKTGDTAYSQKFKGRV
TLTADKSTSTAYMELSSLTSEDTAV YYCTRFY-
SYTYWGQGTLVTVSSGGGGSGGGGSG
GGGDVVMTQSPISLPVTPGEPASIS
CRSSQSLVHSNRN-
TYLHWYLQKPGQSPQLLIYKVSNRFS
GVPDRFSGSSGTDFTLKISR VEAE-
DVGVYYCSQNTHVPPTFGQGTKLEIKTTTPAPRPPT-
PAPTIASQPLSLRPEACRPAA GGAVHIRGLDFACDIYT-
WAPLAGTCGVLLLSLVITLYCKRGRKK
LLYIFKQPFMRPVQT
TQEEDGCSCRFPEEEEGGCELRVKFSRSADAPAY-
OQGQNQLYNELNLGRREEYDVLDK
RRGRDPEMGGKPQRRKNPQEGLYNELQKDK-
MAEAYSEIGMKGERRRGKGHDGLYQG LSTATKDTY-
DALHMQALPPR*), a polypeptide comprising a GC33
anti-GPC3 binding domain, a CD8α hinge and transmem-
brane region, a 4-1BB costimulation endodomain, and a
CD3ζ signaling domain.

In some embodiments, the isolated nucleic acid encoding
an GC33-CD8-BBz polypeptide comprises the sequence of
SEQ ID NO: 21 (ATGTCCOTGCCTACCCAGG
TGCTGGGCCTGCTGCTGCTGTGG
CTGACCGACGCCAGATGCCAAGTGCAGCTGGTCC
AGAGCGGCGCCGAGGT-
GAAAAAGCCTGGCGCCAGCGT-
GAAGGTGTCCTGCAAGGCC TCTGGCTACACCTT-
CACCGACTACGAGATGCACTG
GGTGCGGCAGGCCCCTGGACA GGGCCTGGAATG-
GATGGGCGCTCTGGACCCCAA-
GACCGGCGACACCGCTTATAGCC AGAAGIT-
CAAGGGCAGAGTGACCCTG
ACAGCTGATAAGAGCACAAGCACCGCCTAC ATG-
GAACT-
GAGCAGCCTGACCAGCGAGGACACCGCCGTGTAC-
TACTGCACCAGATT
CTACAGCTACACCTACTGGGGCCAGGGGACCCT
GGTGACAGTGTCTAGCGGTGGAG GTGGATCTG-
GAGGAGGAGGATCCGGTGGAGGAGGTGATGTGGT-
GATGACCCAGAGC CCTCT-
GAGCCTGCCTGTGACCCCTGGA
GAGCCTGCCAGCATCAGCTGCAGAAGCAG
CCAATCTCTGGTGCACAGCAACCGGAACACAT-
ACCTGCACTGGTACCTGCAGAAAC
CTGGCCAGAGCCCCCAGCTGCTGATCTA-
CAAGGTGTCCAACAGATTCAGCGGCGTG CCTGA-
TAGATTCAGCGGATCTGGCAGCGGCACCGACTT-
CACCCTGAAGATCTCTAGA
GTGGAAGCCGAGGACGTGGGCGTGTAC-
TACTGCAGCCAGAACACCCACGTGCCCCC
CACCTTCGGCCAGGGCACAAAGCTGGAAATCAA-
GACCACGACGCCAGCGCCGCGAC CAC-
CAACACCGGCGCCCAC-
CATCGCGTCGCAGCCCCTGTCCCT
GCGCCCAGAGGCGT
GCCGGCCAGCGGCGGGGGGCGCA
GTGCACACGAGGGGGCTGGACTTCGCCTGTGAT
ATCTACATCTGGGCGCCCTTGGCCGGGA
CTTGTGGGGTCCTTCTCCTGTCACTGGTTA
TCACCCTT-
TACTGCAAACGGGGCAGAAAGAAACTCCTGTATAT-
ATTCAAACAACCAT TTATGAGACCAGTACAAAC-
TACTCAAGAGGAAGATGGCTGTA
GCTGCCGATTTCCA GAAGAAGAAGAGGAG-
GATGTGAACTGAGAGTGAAGTTCAGCAG-
GAGCGCAGACG CCCCCGCGTACCAGCAGGGCCAGAACCAGCTC-
TATAACGAGCTCAATCTAGGACGA AGAGAG-
GAGTACGATGTTTTGGACAA-
GACGTGGCCGGGACCCTGAGATGGGGGG
AAAGCCGCAGAGAAGGAAGAACCCTCAG-
GAAGGCCTGTACAATGAACTGCAGAAA GATAA-
GATGGCGGAGGCCTACACTTGAGATTGGGAT-
GAAAGGCGAGCGCCGGAGGG
GCAAGGGGCACGATGGCCTT-
TACCAGGGTCTCAGTACAGCCACCAAGGACACC-
TAC GACGCCCTTCA-
CATGCAGGCCCTGCCCCCTCGCTAA).

In some embodiments, the isolated nucleic acid encodes
SEQ ID NO: 22 (MSVPTQVLGLLLLWLT-
DARCQVQLVQSGALVKKPGASVKVSCK-
ASGYTFTDYEMHW VRQAPGQ-
GLEWMGALDPKTGDTAYSQKFK
GRVTLTADKSTSTAYMELSSLTSEDTAV YYCTRFY-
SYTYWGQGTLVTVSSGGG
GSGGGGSGGGGDVVMTQSPLSLPVTPGEPASIS
CRSSQSLVHSNRNTYLHWYLQKPGQSPQWYKVS
NRFSGVPDRFSGSGSGTDFTLKISR VEAE-
DVGVYYCSQNTHVPPTGQGTKLEIKTTTPAPRPPT-
PAPTIASQPLSLRPEACRPAA GGAVHTRGLD-
FACDIYIWAPLAGTCGVLLLSLV
ITLYCKRGRKKLLYIFKQPFMRPVQT
TQEEDGCSCRFPEEEEGGCELRVKFSRSADAPA-
YQQGQNQLYNELNLGRREEYDVLDK
RRGRDPEMGGKPQRRKNPQEGLYNELQKDK-
MAEAYSEIGMKGERRRGKGHDGLYQG LSTATKDTY-
DALHMQALPPRGSGATNFSLLKQAGDVEENPGP-
MALPVTALLLPLALLLH
AARPNWVNVISDLKKIEDLIQSMHTDAT-
LYTESDVHPSCKVTAMKCFLLELQVISLESGD
ASIHDTVENLILANNSLSSNGNVTESGCKE-
CEELEEKNIKEFLQSFVHIVQMFINTS*), a polypeptide
comprising a GC33 anti-GPC3 binding domain, a CD8α,
hinge and transmembrane region, a 4-1BB costimulation
endodomain, a CD3ζ signaling domain, a furin and P2A
cleavage region, and a secretion signal operably linked to an
IL-15 domain.

In some embodiments, the isolated nucleic acid encoding
a GC33-CD8-BBz-sIL 15 polypeptide comprises the
sequence of SEQ ID NO: 23 (ATGTCCGTGCC-
TACCCAGGTGCTGGGCCTGCTG
CTGCTGTGGCTGACCGACGCCAG ATGC-
CAAGTGCAGCTGGTCCAGAGCGGCGCCGAGGT-
GAAAAAGCCTGGCGCCAGCG
TGAAGGTGTCCTGCAAGGCCTCTGGCTACACCTT-
CACCGACTACGAGATGCACTGGG
TGCGGCAGGCCCCTGGACAGGGCCTGGAATG-
GATGGGCCGCTCTGGACCCCAAGACC
GGCGACACCGCTTATAGCCAGAAGTT-
CAAGGGCAGAGTGACCCTGACAGCTGATAA
GAGCACAAGCACCGCCTACATGGAACT-
GAGCAGCCTGACCAGCGAGGACACCGCCG TGTAC-
TACTGCACCAGATTCTACAGCFACACC-
TACTGGGGCCAGGGGACCCTGGTGA
CAGTGTCTAGCGGTGGAGGTGGATCTGGAGGAG-
GAGGATCCGGTGGAGGAGGTGAT GTGGT-
GATGACCCAGAGCCCFCT-
GAGCCFGCCTGTGACCCCTGGAGAGCCTGCCAGC
ATCAGCTGCAGAAGCAGC-
CAATCTCTGGTGCACAGCAACCGGAACACAT-
ACCTGCA CTGGTACCTGCAGAAACCTGGC
CAGAGCCCCCAGCTGCTGATCTACAAGGTGTCCA
ACAGATTCAGCGGCGTGCCTGATAGATTCAGCG- GATCTGGCAGCGGCACCGACTTC ACCCTGAA-GATCTCTAGAGTG-GAAGCCGAGGACGTGGGCGTGTACTACTGCAGCCA GAACACCCACGTGCCCCC-CACCTTCGGCCAGGGCACAAAGCTGGAAATCAA-GACCA CGACGCCAGCGCCGCGACCAC-CAACACCGGCGCCCACCATCGCGTCGCAGCCCCTG TCCCTGCGCCCAGAGGCGT GCCGGCCAGCGGCGGGGGGC GCAGTGCACACGAGGGG GCTGGACTTCGCCTGT-GATATCTA-CATCTGGGCGCCCTTGGCCGGGACTTGTGGGGT CCTTCTCCTGTCACTGGTFATCACCCTT-TACTGCAAACGGGGCAGAAAGAAACTCCT GTATATATTCAAACAACCATTTATGAGACCAGTA-CAAACTACTCAAGAGGAAGATG GCTGTAGCTGCC-GATTTCCAGAAGAAGAAGAAGGAGGATGTGAACT-GAGAGTGAAG TTCAGCAGGAGCGCA-GACGCCCCGCGTACCAGCAGG GCCAGAACCAGCTCTATAA CGAGCT-CAATCTAGGACGAAGAGAGGAGTAC-GATGTTTGGACAAGAGACGTGGCC GGGACCCT-GAGATGGGGGGAAAGC CGCAGAGAAGGAAGAACCCTCAGGAAGGCCT GTACAATGAACTGCAGAAAGATAAGATGGCG-GAGGCCTACAGTGAGATTGGGATGA AAGGCGAGCGCCGGAGGGGCAAGGGGCAC-GATGGCCTTTACCAGGGTCTCAGTACA GCCAC-CAAGGACACCTACGACGCCCITCA-CATGCAGGCCCTGCCCCCTCGCGGTAGC GGGGCTACGAACTTCTCCCTTCTTAAACAAGCGG-GAGACGTGGAAGAAAATCCCGG ACCTATGGCCT-TACCAGTGACCGCCTTGC TCCTGCCGCTGGCCTTGCTGCTCCACGCC GCCAGGCCGAACTGGGTGAATGTAATAAGTGATTT-GAAAAAAATTGAAGATCTTAT TCAATCTATGCATAT-TGATGCTACTTATATACGGAAAGTGATGTT-CACCCCAGTTGC AAAGTAACAGCAATGAAGTGCTTTCTCTTGGAGT-TACAAGTTATTTCACTTGAGTCC GGAGATGCAAGT-ATTCATGATACAGTAGAAAATCTGAT-CATCCTAGCAAACAACAG TTTGTCTTCTAATGGGAATGTAACAGAATCTG-GATGCAAAGAATGTGAGGAACTGG AGGAAAAAAATATTAAAGAAT-TTTTGCAGAGTTTTGTACATATTGTCCAAATGTTCA TCAACACTTCTTGA).

In some embodiments, the isolated nucleic acid encoding a GC33-CD8-BBz-sIL15 polypeptide comprises the sequence of SEQ ID NO: 24 (ATGTCCGTGCC-TACCCAGGTGCTGGGCCTGC TGCTGCTGTGGCTGACCGACGCCAG ATGC-CAAGTGCAGCTGGTCCAGAGCGGCGCCGAGGT-GAAAAAGCCTGGCGCCAGCG TGAAGGTGTCCTGCAAGGCCTCTGGCTACACCTT-CACCGACTACGAGATGCACTGGG TGCGGCAGGCCCCTGGACAGGGCCTGGAATG-GATGGGCGCTCTGGACCCCAAGACC GGCGACACCGCTTATAGCCAGAAGTT-CAAGGGCAGAGTGACCCTGACAGCTGATAA GAGCACAAGCACCGCCIACATGGAACT-GAGCAGCCTGACCAGCGAGGACACCGCCG TGTAC-TACTGCACCAGATTCTACAGCTACACC-TACTGGGGCCAGGGGACCCTGGTGA CAGTGTCTAGCGGTGGAGGTGGATCTGGAGGAG-GAGGATCCGGTGGAGGAGGTGAT GTGGT- GATGACCCAGAGCCCTCT-GAGCCTGCCTGTGACCCCTGGAGAGCCTGCCAGC ATCAGCTGCAGAAGCAGC-CAATCTCTGGTGCACAGCAACCGGAACACAT-ACCTGCA CTGGTACCTGCAGAAACCT GGCCAGAGCCCCCAGCTGCTGATCTA-CAAGGTGTCCA ACAGATTCAGCGGCGTGCCTGA-TAGATTCAGCGGATCTGGCAGCGGCACCGACTTC ACCCTGAAGATCTCTAGAGTG-GAAGCCGAGGACGTGGGCGTGTAC-TACTGCAGCCA GAACACCCACGTGCCCCC-CACCTTCGGCCAGGGC ACAAAGCTGGAAATCAAGACCA CGACGCCAGCGCCGCGACCACCAACACCGGCGCC-CACCATCGCGTCGCAGCCCCTG TCCCTGCGCCCAGAGGCGTG CCGGCCAGCGGCGGGGGGCG CAGTGCACACGAGGGG GCTGGACTTCGCCTGTGA-TATCTA-CATCTGGGCGCCCTTGGCCGGGACTTGTGGGGT CCTTCTCCTGTCACTGGTTATCACCCT-TACTGCAAACGGGGCAGAAAGAAACTCCT GTATATATTCAAACAACCATTTATGAGACCAGTA-CAAACTACTCAAGAGGAAGATG GCTGTAGCTGCC-GATTFCCAGAAGAAGAAGAAGGAGGATGTGAACT-GAGAGTGAAG TTCAGCAGGAGCGCA-GACGCCCCGCGTACCAGCA GGGCCAGAACCAGCTCTATAA CGAGCT-CAATCTAGGACGAAGAGAGGAGTAC-GATGTTTTGGACAAGAGACGTGGCC GGGACCCT-GAGATGGGGGGAAAGCCGCAG AGAAGGAAGAACCCTCAGGAAGGCCT GTACAAT-GAACTGCAGAAAGATAAGATGGCGGAGGCCTA-CAGTGAGATTGGGATGA AAGGCGAGCGCCG-GAGGGGCAAGGGGCACGA TGGCCTTTACCAGGGTCTCAGTACA GCCAC-CAAGGACACCTACGACGCCCTTCA-CATGCAGGCCCTGCCCCCTCGCGGTAGC GGGGC-TACGAACTTCTCCCTTCTTA AACAAGCGGGAGACGTGGAAGAAAATCCCGG ACCTATGGCCTTACCAGTGACCGCCTTGCTC CTGCCGCTGGCCTTGCTGCTCCACGCC GCCAGGCCGAACTGGGTGAATGTGATCAGCGATCT-GAAGAAGATCGAGGATCTGAT CCAGTCCATGCA-CATCGATGCCACCCTGTATACCGAGAGC-GATGTGCACCCCAGCTG CAAGGTGACCGCCATGAAGTGCTTTCTGCTG-GAGCTGCAGGIGATCTCCCTGGAGTC CGGAGATGCCAGCATCCACGATACCGTG-GAGAATCTGATCATCCTGGCCAACAACA GCCTGTCCTCCAATGGCAATGTGACCGAGTCGG-GATGCAAGGAGTGCGAGGAGCTG GAG-GAGAAGAATATCAAGGAGTTTCTGCAGAG CTTTGTACATATTGTCCAAATGTTC ATCAACACTTCTTGA).

In some embodiments, the isolated nucleic acid is a linear nucleic acid. In some embodiments, the isolated nucleic acid is a vector, such as a plasmid vector, an adenoviral vector, an adeno-associated viral vector, a viral vector, a retroviral vector (e.g, a gamma retroviral vector), or a lentiviral vector. In some embodiments, the isolated nucleic acid, or an, e.g., contiguous, portion thereof containing the binding domain transmembrane domain and one or more signaling and/or costimulation endodomains is integrated into the genome of a host cell, such as a host γδ T cell. In an exemplary embodiment, the isolated nucleic acid is retroviral vector.

γδ T Cells:

Aspects of the invention include γδ T cells that functionally express an isolated nucleic acid described herein, and thereby expresses a CAR on the surface of the γδ T cell.

Aspects of the invention can additionally or alternatively include γδ T cells having in vitro or in vivo cytotoxic activity against a solid tumor cell that exhibits cell surface expression of the tumor associated antigen (TAA). In some cases, the cytotoxic activity is innate activity. In some cases, the cytotoxicity is at least in part, significantly (>about 25%), or entirely, due to the presence of a CAR construct having a binding domain that specifically binds the TAA expressed on the surface of the solid tumor cell. In some cases, the γδ T cells exhibit solid tumor cell killing activity of said γδ T cell is greater than an innate level of in vitro and/or in vivo solid tumor cell killing activity in a control γδ T cell. In some cases, the control γδ T cell does not comprise a CAR construct. in some cases, the control γδ T cell comprises a CAR construct lacking a binding domain described herein, a hinge region described herein, a transmembrane domain described herein, a signaling domain described herein, and/or a costimulation endodomain described herein.

In some cases, the cytotoxicity is at least in part, significantly (>about 25%) or entirely, due to the presence of a CAR construct having a binding domain that specifically binds TyrD or an epitope within TyrD, such as TyrD$_{369-377}$. In some cases, the cytotoxicity is at least in part, significantly (>about 25%), or entirely, due to the presence of a CAR construct having a binding domain that specifically binds TyrD or an epitope within TyrD, such as TyrD$_{369-377}$ in an HLA restricted (e.g., class I HLA-restricted) manner. In some cases, the cytotoxicity is at least in part, significantly (>about 25%), or entirely, due to the presence of a CAR. construct having a binding domain that specifically binds HLA-A2/TyrD$_{369-377}$. In some cases, the γδ T cells functionally express a CAR encoded by an isolated nucleic acid described herein that specifically binds TyrD or a peptide fragment thereof.

In some embodiments, γδ T cells described herein can exhibit HLA-restricted HLA class I restricted) cytotoxicity. In other embodiments, most (>50%), substantially all (>90%), or all of the cytotoxic activity is not HLA-restricted (e.g., HLA class I restricted). HLA-restricted cytotoxic activity can be assessed by comparing in vitro cytotoxicity against an HLA (e.g., HLA class I) (null) tumor cell line versus in vitro cytotoxicity against an HLA+ (e.g., HLA class I$^+$) tumor cell line. In some embodiments, the HLA-restricted cytotoxic activity is at least in part, significantly (>25%), or entirely, provided by the use of a T cell Receptor-like binding domain. T cell receptor like binding domains are binding domains that specifically recognize the antigen when presented on the surface of a cell in complex with an MHC molecule. T cell Receptor-like binding domains are further described, e.g., in WO 2016/199141.

γδ T cells described herein can exhibit robust and/or persistent solid tumor cell killing activity. In some cases, the solid tumor cell killing activity can persist for at least about 6 days to 120 days, or for at least about 6 days to 180 days, from first contact with a solid tumor cell. In some cases, the solid tumor cell killing activity of a γδ T cell described herein, or a progeny thereof, can persist for at least about 6 days to 120 days, or for at least about 6 days to 180 days, from first contact with a solid tumor cell, or from administration of the γδ T cell described herein. This persistent solid tumor cell killing activity can be exhibited in vitro, in vivo, or both in vitro and in vivo.

Aspects of the invention can additionally or alternatively include γδ T cells that proliferate in response to contact with cells that exhibit cell surface expression, or overexpression, of the tumor associated antigen (TAA). The cells that exhibit cell surface expression of the tumor associated antigen (TAA) can be normal cells, such as normal endothelial cells. The cells that exhibit cell surface expression, or overexpression, of the tumor associated antigen (TAA) can be solid tumor cells. In some cases, the proliferation is an innate activity. In some eases, the proliferation is at least in part, significantly (>about 20% or >about 25%), or entirely, due to the presence of a CAR construct having a binding domain that specifically binds the IAA expressed on the surface of the cell. In some cases, the γδ T cells exhibit a greater level of in vitro and/or in vivo proliferation as compared to a control γδ cell. In some cases, the control γδ T cell does not comprise a CAR construct. In some cases, the control γδ T cell comprises a CAR construct lacking a binding domain described herein, a hinge region described herein, a transmembrane domain described herein, a signaling domain described herein, and/or a costimulation endodomain described herein.

In some cases, the proliferation is at least in part, significantly (>about 20 or >about 25%), or entirely, due to the presence of a CAR construct having a binding domain that specifically binds TyrD or an epitope within TyrD. In some cases, γδ T cells exhibiting proliferation in response to contact with a cell that exhibits cell surface expression of TyrD functionally express a TyrD-specific CAR encoded by an isolated nucleic acid described herein.

γδ T cells described herein can exhibit robust and/or persistent proliferation in a host organism that comprises the cell that exhibits cell surface expression, or overexpression, of the tumor associated antigen (TAA). In some cases, the proliferation can persist for at least about 6 days to 120 days, or for at least about 6 days to 180 days, from first contact with a cell that exhibits cell surface expression, or overexpression, of the tumor associated antigen (TAA) or from a date of administration of the γδ T cell to the host organism. In some cases, the proliferation of a γδ T cell described herein, or a progeny thereof, in the host organism that comprises the cell that exhibits cell surface expression, or overexpression, of the tumor associated antigen (TAA) can persist for at least about 6 days to 120 days, or for at least about 6 days to 180 days, from first contact with the cell or from the date of first administration of the γδ T cell to the host organism. In some cases, the proliferation in the host organism is at least in part, significantly (>about 20% or >about 25%), or entirely, due to the presence of a CAR construct having a binding domain that specifically binds TyrD or an epitope within TyrD. In some cases, γδ T cells exhibiting proliferation in the host organism comprising a cell that exhibits cell surface expression of TyrD functionally express a TyrD specific CAR encoded by an isolated nucleic acid described herein.

In some embodiments, the γδ T cells described herein express, or persistently express, pro-inflammatory cytokines such as tumor necrosis factor alpha or interferon gamma after contact with the cell that expresses or over expresses TyrD or a peptide fragment thereof on the surface of the cell. In some embodiments, the γδ T cells described herein, or progeny thereof, express, or persistently express, pro-inflammatory cytokines such as tumor necrosis factor alpha or interferon gamma after contact with the cell that expresses or over expresses TyrD or a peptide fragment thereof on the surface of the cell, e.g., in a host organism comprising the cell that expresses or over expresses TyrD or a peptide fragment thereof on the surface of the cell.

In some embodiments, the γδ T cell, or a pharmaceutical composition containing the γδ T cell, exhibits essentially no, or no graft versus host response when introduced into an allogeneic host. In some embodiments, the γδ T cell, or a pharmaceutical composition containing the γδ T cell, exhibits a clinically acceptable level of graft versus host response when introduced into an allogeneic host. In some embodiments, a clinically acceptable level is an amount of graft versus host response that does not require cessation of a γδ T cell treatment to achieve a therapeutically effective treatment. In some embodiments, a clinically acceptable level of graft versus host response (GvHD) is an acute response that is less severe than Grade C according to an applicable IBMTR grading scale. The severity of acute graft versus host response is determined by an assessment of the degree of involvement of the skin, liver, and gastrointestinal tract. The stages of individual organ involvement are combined to produce an overall grade, which has prognostic significance. Grade I(A) GvHD is characterized as mild disease, grade II(B) GvHD as moderate, grade III(C) as severe, and grade IV(D) life-threatening. The IBMTR grading system defines the severity of acute GvHD as follows (Rowlings et al., Br J Haematol 1997; 97:855):

Grade A—Stage 1 skin involvement alone (maculopapular rash over <25 percent of the body) with no liver or gastrointestinal involvement Grade B—Stage 2 skin involvement; Stage 1 to 2 gut or liver involvement Grade C—Stage 3 involvement of any organ system (generalized erythroderma; bilirubin 6.1 to 15.0 mg/dL; diarrhea 1500 to 2000 mL/day)

Grade D—Stage 4 involvement of any organ system (generalized erythroderma with bullous formation; bilirubin >15 mg/dL; diarrhea >2000 mL/day OR pain OR ileus)

See also, Schoemans et al., *Bone Marrow Transplantation* volume 53, pages 1401-1415 (2018), e.g., at Tables 1 and 2, which discloses criteria for assessing and grading acute GvHD.

In some embodiments, the γδ T cell, or a pharmaceutical composition containing the γδ T cell, exhibits reduced or substantially reduced graft versus host response when introduced into an allogeneic host as compared to a graft versus host response exhibited by control αβ T cells, or a control pharmaceutical composition comprising the control αβ T cells, administered to an allogeneic host. In some cases, the control αβ T cell is an allogeneic non-engineered control αβ T cell. In some cases, the control αβ T cell does not comprise a CAR or does not comprise the same CAR as a reference γδ T cell.

The γδ T cells described herein can be δ1, δ2, δ3, or δ4 γδ T cells, or combinations thereof In some cases, the γδ T cells are mostly (>50%), substantially (>90%), essentially all, or entirely δ2⁻ γδ T cells. In some cases, the γδ T cells are mostly (>50%), substantially (>90%), essentially all, or entirely δ1 γδ T cells.

γδ T cells can be obtained from an allogeneic or an autologous donor. The γδ T cells can be, partially or entirely purified, or not purified, and expanded ex vivo. Methods and compositions for ex vivo expansion include, without limitation, those described in WO 2017/197347 The expansion may be performed before or after, or before and after, a CAR construct is introduced into the γδ T cell(s).

γδ T cells described herein can be stored, e.g., cryopreserved, for use in adoptive cell transfer.

Methods of Inhibiting or Killing Tumor Cells

One or multiple non-engineered, γδ T-cell populations, engineered, γδ T-cell populations, and/or admixtures thereof, having cytotoxic activity against a solid tumor cell can he administered to a subject in any order or simultaneously. If simultaneously, the multiple non-engineered, γδ T-cell. population, engineered, γδ T-cell population, and/or admixtures thereof, of the invention can be provided in a single, unified form, such as an intravenous injection, or in multiple forms, for example, as multiple intravenous infusions, s.c, injections or pills. The non-engineered, γδ T-cell population, engineered, γδ T-cell population, and/or admixtures thereof, of the invention can be packed together or separately, in a single package or in a plurality of packages. One or all of the non-engineered γδ T-cell population, engineered γδ T-cell population, and/or admixtures thereof, of the invention can be given in multiple doses. If not simultaneous, the timing between the multiple doses may vary to as much as about a week, a month, two months, three months, four months, five months, six months, or about a year. In some cases, a non-engineered, enriched γδ T-cell population, an engineered, enriched γδ T-cell population, and/or admixtures thereof, of the invention can proliferate within a subject's body, in vivo, after administration to a subject. One or more non-engineered γδ T-cell populations, one or more engineered γδ T-cell populations, and/or admixtures thereof, can be frozen to provide cells for multiple treatments with the same cell preparation. One or more non-engineered γδ T-cell populations, one or more engineered γδ T-cell populations, and/or admixtures thereof, of the disclosure, and pharmaceutical compositions comprising the same, can be packaged as a kit. A kit may include instructions (e.g., written instructions) on the use of the non-engineered γδ T-cell population, the engineered γδ T-cell population, and/or admixtures thereof, and compositions comprising the same.

In some cases, a method of treating a solid cancer comprises administering to a subject a therapeutically-effective amount of a non-engineered γδ T-cell population, an engineered γδ T-cell population, andlor admixtures thereof, wherein the administration treats the solid cancer. In some embodiments the therapeutically-effective amount of the non-engineered, γδ T-cell population, the engineered γδ T-cell population, and/or admixtures thereof, is administered for at least about 10 seconds, 30 seconds, 1 minute, 10 minutes, 30 minutes, 1 hour. 2 hours, 3 hours, 4 hours, 5 hours, 8 hours, 12 hours, 24 hours, 2 days, 3 days, 4 days, 5 days, 6 days, 1 week, 2 weeks, 3 weeks, 1 month, 2 months, 3 months, 4 months, 5 months, 6 months, or 1 year. In some embodiments the therapeutically-effective amount of the non-engineered γδ T-cell population, the engineered γδ T-cell population, and/or admixtures thereof, is administered for at least one week. In some embodiments the therapeutically-effective amount of the non-engineered γδ T-cell population, the engineered γδ T-cell population, and/or admixtures thereof, is administered for at least two weeks.

A non-engineered γδ T-cell population, an engineered γδ T-cell population, and/or admixtures thereof, described herein can be administered before, during, or after the occurrence of a disease or condition, and the timing of administering a pharmaceutical composition containing the γδ T-cell population can vary. For example, the γδ T-cell population can be used as a prophylactic and can be administered continuously to subjects with a propensity to conditions or diseases in order to lessen a likelihood of the occurrence of the disease or condition. The initial administration can he via any route practical, such as by any route described herein using any formulation described herein. In some examples, the administration of a γδ T-cell population of the disclosure is an intravenous administration. One or multiple dosages of the γδ T-cell population can be administered as soon as is practicable after the onset of a solid cancer and for a length of time necessary for the treatment of the immune disease, such as, for example, from about 24 hours to about 48 hours, from about 48 hours to about 1 week, from about 1 week to about 2 weeks, from about 2 weeks to about 1 month, from about 1 month to about 3 months. In some embodiments, one or multiple dosages of the γδ T-cell population can be administered years after onset of the cancer and before or after other treatments.

In some embodiments, the γδ T-cell population is administered simultaneously or sequentially with one or more methods to elevate common gamma chain cytokine(s). As used herein, "one or more methods to elevate common gamma chain cytokinets): refers to a method, or combination of methods, that alters the physiological state of a subject, such that at least one common gamma chain cytokine level is elevated in the subject. In some embodiments, the method elevates the level of one or more common gamma chain cytokine(s) selected from the group consisting of IL-2, IL-7, and IL-15, preferably wherein the method elevates the level of IL-15 in the subject. In some embodiments, the method comprises lymphodepletion. In some embodiments, the method comprises administering one or more common gamma chain cytokine(s) to the subject. In some cases, IL-2, IL-7, and/or IL-15, preferably IL-15, are administered. In some embodiments, the method comprises secreting common gamma chain cytokine(s) from an administered, e.g., γδ T, cell. In some cases, IL-2, IL-7, and/or IL-15, preferably IL-15, are secreted.

In some embodiments, the administering one or more methods to elevate common gamma chain cytokine(s) comprises lymphodepletion before introducing the γδ T cell(s). In some embodiments, the administering one or more methods to elevate common gamma chain cytokine(s) comprises administering simultaneously with introducing the γδ T cell(s) or sequentially an amount of common gamma chain cytokine(s) effective to increase proliferation, cytotoxic activity, persistence, or the combination thereof of the introduced γδ T cell(s), preferably wherein the method comprises administering IL-2 or one or more mimetics thereof, more preferably wherein the method comprises administering IL-15 or one or more mimetics thereof. The amount of administered common gamma chain cytokine(s) can be an amount effective to increase proliferation, cytotoxic activity, persistence, or the combination thereof of the introduced γδ T cell(s) before and/or after introducing the γδ T cell(s). Exemplary amounts of IL-15 include, without limitation between 0.01-10 μg/kg/dose every 24 hours. Exemplary amounts of IL-2 include, without limitation, between about $3\times10^6$ and about $22\times10^6$ units every 8-48 hours. For example, the dosing regimen for IL2 in RCC is 600,000 International Units/kg (0.037 mg/kg) IV q8 hr infused over 15 minutes for a maximum 14 doses.

In some embodiments, the administering one or more methods to elevate common gamma chain cytokinc(s) comprises lymphodepletion before administering the γδ cell(s) and administering simultaneously with introducing the γδ T cell(s) or sequentially an amount of common gamma chain cytokine(s) effective to increase proliferation, cytotoxic activity, persistence, or the combination thereof of the introduced γδ T cell(s).

EXAMPLES

Example 1

Figure 2:
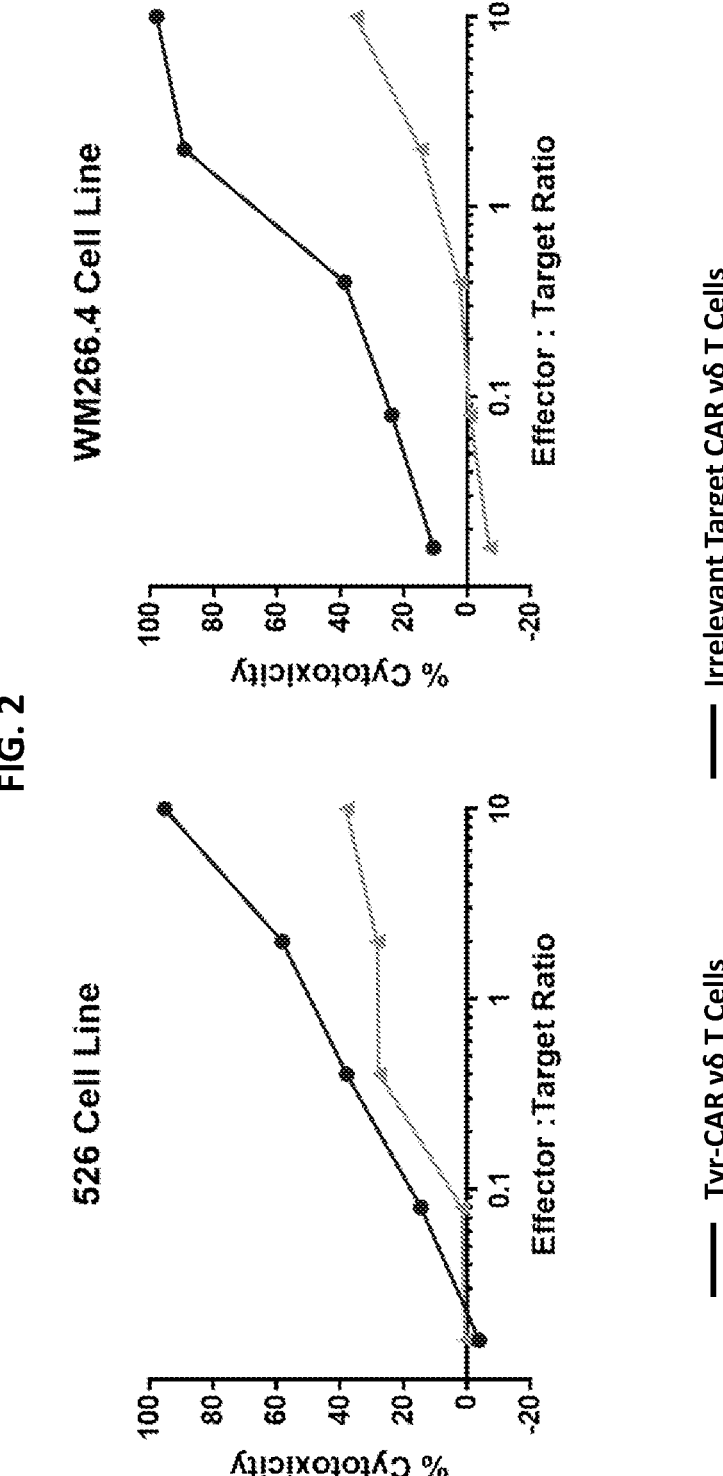
FIG. 2 illustrates in vitro cytotoxicity of engineered and non-engineered γδ T cells described herein against 526 and WM266.1-Luc melanoma cell lines.

Human PBMCs at $1\times10^6$/mL in a modified culture media were activated on pre-coated with anti-VM antibody D1-08 or D1-35 for 5 days in the presence of IL-2 (100 U/mL) in 24-well plates (Costar). On day 5, cell cultures were transduced with γ-retroviral constructs encoding an anti-TyrD chimeric antigen receptor (SEQ ID NO:8) in the presence of retronectin. On day 6 cells were returned to the modified culture media and further expanded with feeding and IL-2 replacement as needed. On days 17, 18 or 19, cells were harvested, and remaining αβ T cells were depleted using AutoMACS® kit (Miltenyi Biotec). Purity of γδ cell population and transduction efficiency was assessed by FACS. In parallel, untransduced cell cultures were expanded in the same manner, without adding the retrovirai supernatant. As shown in FIG. 2, untransduced expanded Vδ1 cells elicited some degree of cytotoxicity against 526 and WM266.1.-Luc melanoma cell line that are known to express Tyrosinase and present the Tyr369-377 peptide. This cytotoxicity was augmented by introduction of an anti-TyrD CAR. Cytotoxicity was determined by total luminescence measurement in 96-well plates, by adding luminescent substrate D-Luciferin (Perkin Elmer) after 18 hr co-incubation at inideated E/T ratios

Example 2

Figure 3:
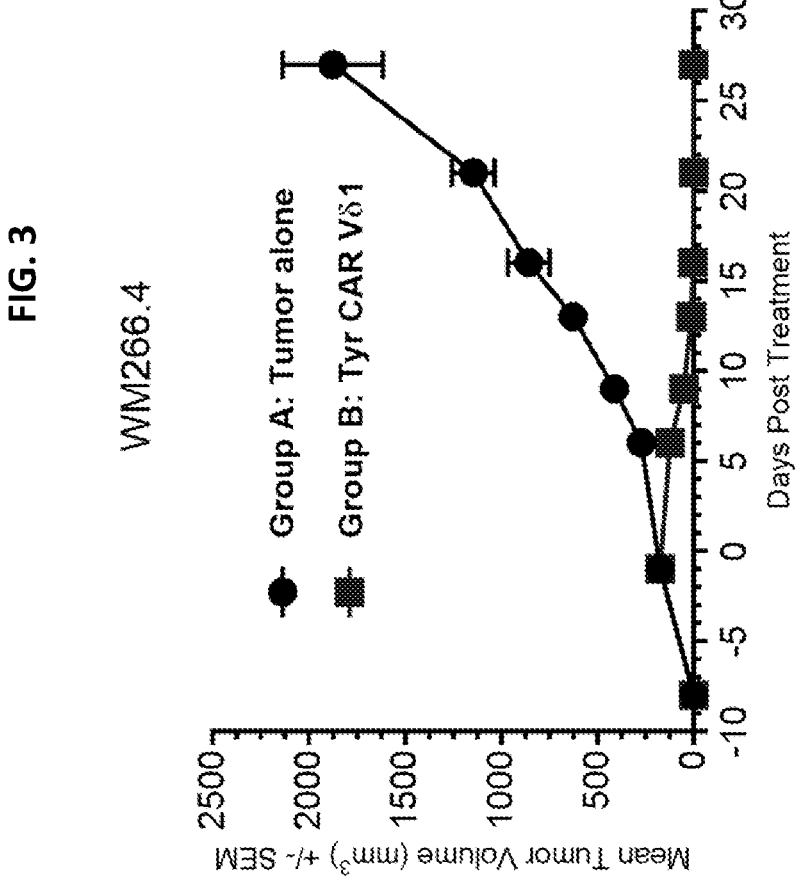
FIG. 3 illustrates in vivo therapeutic efficacy of γδ T cells described herein in a subcutaneous WM266.4 cell NOD scid gamma (NSG) mouse model.

WM266.4-Luc cells ($4\times10^6$ per animal) were subcutaneously implanted into NSG mice (Jackson Labs). When tumors reached 100-200 mm³ size, animals were treated with $6\times10^6$ anti-TyrD CAR+ Vδ1 cells. Animals were dosed concomitantly with IL-2 (60,000 U/dose) 3 times a week throughout the study. The results are illustrated in FIG. 3. As shown in FIG. 3, the animals administered the anti-TyrD CAR+ Vδ1 cells exhibited robust control of tumor burden.

Example 3

Figure 5:
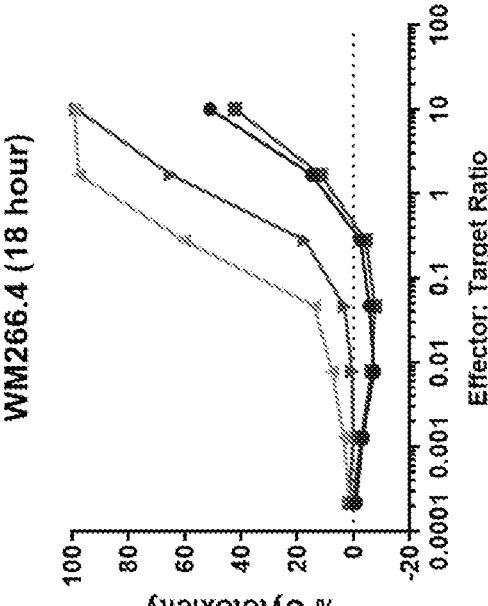
FIG. 5 illustrates cytotoxic activity of Vδ1 T cells transduced with control CAR constructs or constructs targeting the tyrosinase polypeptide.

Tyr CAR constructs were introduced into Vδ1 T cells as described above and cells were expanded and tested in cytotoxicity assay against WM266.4-Luc cells. Control, non-TyrD targeting CAR constructs were used as control. The results are illustrated in FIG. 5 and show the increased cytotoxicity afforded by the anti-TyrD CAR constructs.

Example 4

Human PBMCs at $1\times10^6$/mL in growth media were activated in a 24-well plate (Costar) pre-coated with anti-Vδ1 antibody D1-08 or D1-35 for 5 days in the presence of IL-2 (100 U/mL). On day 5, cell cultures were transduced with γ-retroviral constructs encoding anti-GPC3 chimeric antigen receptor (SEQ ID NO: 20 (GC33 CAR) or SEQ ID NO: 22 (GC33 CAR +sIL15 and GC33 CAR+CO sIL15) in the presence of retronectin. GC33 CAR is encoded by the nucleic acid. sequence of SEQ ID NO:21; GC33 CAR+ sIL15 is encoded by the nucleic acid. sequence SEQ ID NO: 23; GC33 CAR+CO SIL15 includes a codon optimized sIL15 encoding region and is encoded by the nucleic acid sequence of SEQ ID NO: 24. On day 6 cells were returned to growth media and further expanded with feeding and IL-2 replacement as needed. On days 17, 18 or 19, cells were harvested, and remaining αβ T cells were depleted using AutoMACS® kit (Miltenyi Biotec). Purity of γδ cell population and transduction efficiency was assessed by FACS (FIG. 6). Briefly, CAR-T cells were stained by incubating cells with 1 μg/mL of soluble recombinant biotinylated GPC3 (R&D Systems). Detection of binding was performed using streptavidin-PE at the manufacturer-suggested dilution of 1:500.

Figure 7:
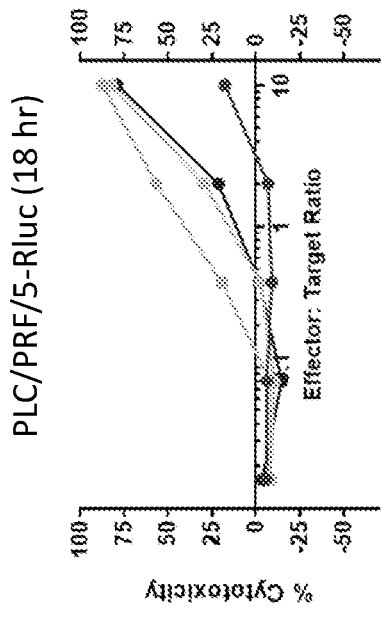
FIG. 7 illustrates cytotoxic activity of Vδ1 T cells either untransduced or transduced with anti-GPC3 CAR. constructs against a panel of liver cancer cell line with different levels of GPC3 expression.
Figure 7:
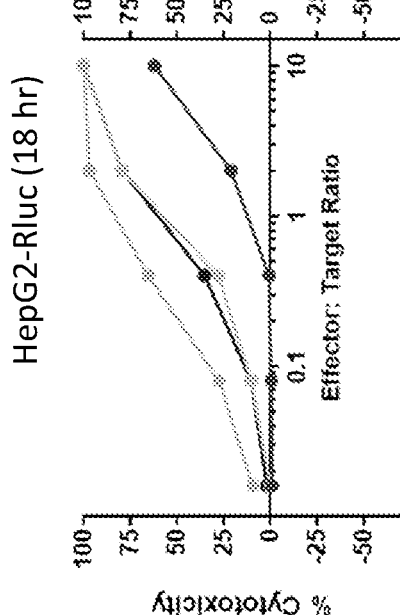
Figure 7:
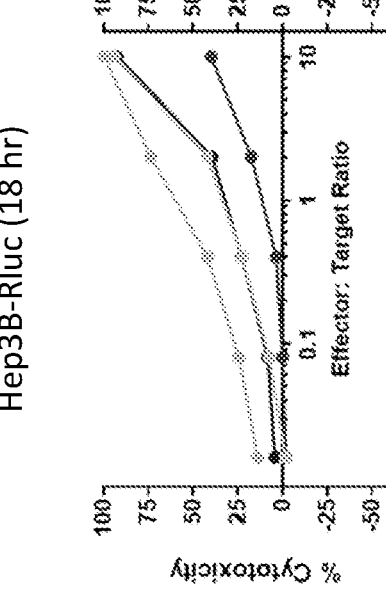

In parallel, untransduced cell cultures were expanded in the same manner, without adding the retroviral supernatant. Expanded cells were tested in the in vitro cytotoxicity assay on GPC3 positive (HepG2, Hep3B, PLC/PRF/5). As shown in FIG. 7, untransduced expanded VM cells elicit some degree of cytotoxicity against liver cancer cell lines that are known to express GPC3. This cytotoxicity is potentiated by introduction of GPC3 CAR, with or without sIL15 cytokine engineered to he expressed in tandem. Cytotoxicity was determined by total luminescence measurement in 96-well plates, by adding luminescent substrate D-Luciferin (Perkin Elmer) after 18 h co-incubation at indicated E/T ratios.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles and aspects of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary aspects shown and described herein. Rather, the scope and spirit of present invention is embodied by the appended claims.

---

The invention claimed is:

1. A δ1 γδ T cell comprising:

a. a nucleic acid encoding a chimeric antigen receptor (CAR), wherein the CAR comprises:

(i) a binding domain that specifically binds to GPC3;

(ii) a CD8α hinge domain;

(111) a CD8α transmembrane domain;

(iv) a costimulatory signaling region selected from a 4-1BB costimulatory signaling region and a CD27 costimulatory signaling region; and (v) a CD3ζ C. signaling domain: or b. a polypeptide comprising a CAR comprising an amino acid sequence encoded by the nucleic acid of (a);

wherein the δ1 γδ T cell functionally expresses the binding domain of the polypeptide or the nucleic acid encoded CAR on the surface of the δ1 γδ T cell, and wherein the nucleic acid encodes SEQ ID NO: 20.

2. The δ1 γδ T cell of claim 1, wherein the (i)-(v) are in 5' to 3' order.

3. The δ1 γδ T cell of claim 1, wherein the CAR comprises:

a. a CD8α hinge domain comprising SEQ ID NO:1 (PTPAPTIASQPLSLRPEACRPAAGGAVHTRGLD-FACDIY) or SEQ ID NO:2 (TTTPAPRPPTPAPTIA-SQPLSLRPEACRPAAGGAVHTRGLDFACDIY);

b. a CD8α transmembrane domain comprising SEQ ID NO:3 (IWAPLAGTCGVLLLSLVITLYC); and/or c. a CD35ζ signaling domain comprising:

```
(i)
                                        SEQ ID NO: 4
(RVKFSRSADAPAYQQGQNQLYNELNLGRREEYD

VLDKRRGRDPEMGGKPQRRKNPQEGLYNELQKDK

MAEAYSEIGMKGERRRGKGHDGLYQGLSTATKDT

YDALHMQALPPR);
or (ii)
                                        SEQ ID NO: 5
(RVKFSRSADAPAYQQGQNQLYNELNLGRREEYD

VLDKRRGRDPEMGGKPRRKNPQEGLYNELQKDKM

AEAYSEIGMKGERRRGKGHDGLYQGLSTATKDTY

DALHMQALPPR).
```

4. The δ1 γδ T cell of claim 3, wherein the CAR comprises:

a. a 4-1BB costimulatory signaling region comprising SEQ ID NO:6 (KRGRKKLLY-IFKQPFMRPVQTTQEEDGCSCRFPEEEEGGCEL); or b. a CD27 costimulatory signaling region comprising SEQ ID NO:7 (QRRKYRSNKGESPVEPAEPCHY-SCPREEEGSTIPIQEDYRKPEPACSP), or wherein the nucleic acid encodes the 4-1BB costimulatory signaling region comprising SEQ ID NO:6 and the CD27 costimulatory signaling region comprising SEQ ID NO:7.

5. The δ1 γδ T cell of claim 1, wherein the nucleic acid further encodes:

a. a secreted cytokine;

b. a secreted common gamma chain interleukin;

c. a secreted IL-15;or d. a secreted common gamma chain interleukin, and a multi-cistronic linker region amino terminal to the interleukin or interleukin secretion signal.

6. The δ1 γδ T cell of claim 5, wherein:

a. the secretion signal comprises a sequence of SEQ ID NO: 12 or SEQ ID NO: 26;

b. the sIL15 domain comprises a sequence of SEQ ID NO: 14;

c. the P2A cleavage sequence comprises a sequence of SEQ ID NO: 15 or SEQ ID NO: 25;

d. the furin cleavage sequence comprises a sequence of SEQ ID NO: 16; and/or e. the CAR comprises, in amino to carboxy order, a sequence of SEQ ID NO: 17, SEQ ID NO: 12, and SEQ ID NO: 14.

7. The δ1 γδ T cell of claim 1, wherein the nucleic acid comprises the sequence of SEQ ID NO: 21.

8. A cell population comprising a plurality of δ1 γδ T cells according to claim 1.

9. The cell population of claim 8, wherein the plurality comprises at least about $10^8$ δ1 γδ T cells, or from about $10^8$ δ1 γδ T cells to about $10^{11}$ δ1 γδ T cells.

10. The cell population of claim 8, wherein the plurality comprises a composition that is at least 60%, 80%, or from about 60% or 80% to about 90% or 95% δ1 γδ T cells.

11. A method of making the δ1 γδ T cell of claim 1, or the cell population of claim 8, wherein the method comprises transfecting δ1 γδ T cell(s) with the nucleic acid according to claim 1.

12. The method of claim 11, wherein the method comprises retroviral transduction.

13. The method of claim 11, wherein the method comprises ex vivo expansion of the δ1 γδ T cell(s), wherein the ex vivo expansion is performed before transfection and/or after transfection of the nucleic acid.

14. A pharmaceutical composition comprising a pharmaceutically acceptable excipient and a δ1 γδ T cell of claim 1 or the cell population of claim 8.

15. A method of killing a solid tumor cell that exhibits cell surface expression of GPC3, the method comprising contacting the solid tumor cell with a tumor cell killing effective amount of the δ1 γδ T cell of claim 1; the cell population of claim 8; or the pharmaceutical composition of claim 14.

16. The method of claim 15, wherein the method comprises introducing a therapeutically effective amount of the δ1 γδ T cell(s) or the pharmaceutical composition into a host organism comprising the solid tumor cell.

17. The method of claim 16, wherein the method comprises introducing into a host organism comprising the solid tumor cell a therapeutically effective amount of the δ1 γδ T cell(s) or the pharmaceutical composition and simultaneously or sequentially administering one or more methods to elevate common gamma chain cytokine(s).

18. The method of claim 17, wherein the administering one or more methods to elevate common gamma chain cytokine(s) comprises administering simultaneously with introducing the δ1 γδ T cell(s) or sequentially an amount of common gamma chain cytokine(s) effective to increase proliferation, cytotoxic activity, persistence, or the combination thereof of the introduced δ1 γδ T cell(s).

19. The method of claim 18, wherein the one or more methods to elevate common gamma chain cytokine(s) comprise administering an amount of common gamma chain cytokine(s) effective to increase proliferation, cytotoxic activity, persistence, or the combination thereof of the introduced δ1 γδ T cell(s) before and/or after introducing the γδ T cell(s).

20. The method of claim 17, wherein the one or more methods to elevate common gamma chain cytokine(s) comprises lymphodepletion before introducing the δ1 γδ T cell(s).

21. The method of claim 17, wherein the one or more methods to elevate common gamma chain cytokine(s) comprises secretion of one or more common gamma chain cytokine(s) from the introduced δ1 γδ T cell(s).

22. The method of claim 16, wherein the method reduces the in vivo tumor burden in the host organism, and/or increases the mean survival time of the host organism as compared to a control organism, wherein the control organism is not treated with the δ1 γδ T cell(s) or the pharmaceutical composition.

23. The method of claim 15, wherein the method is a method of treating cancer in a subject in need thereof.

24. A method of treating cancer in a subject in need thereof, the method comprising administering a therapeutically effective amount of δ1 γδ T cells according to claim 1, wherein the cancer comprises solid tumor cells that exhibit cell surface expression of GPC3.

25. The method of claim 24, wherein the method comprises simultaneously with the administering of δ1 γδ T cells or sequentially, administering one or more methods to elevate common gamma chain cytokine(s).

26. The method of claim 24, wherein the method comprises performing a plurality of administrations of the δ1 γδ T cells, wherein the interval between the plurality of administrations is at least about a week, or at least about 2, 3, 4, 5, 6, 7, 8, or 12 weeks, and/or no more than once every 6 or 12 months.

27. The δ1 γδ T cell of claim 1, wherein the nucleic acid encodes SEQ ID NO: 20.

28. The δ1 γδ T cell of claim 27, wherein the nucleic acid comprises the sequence of SEQ ID NO: 23 or 24.

29. The δ1 γδ T cell of claim 3, wherein the IL-15 in c comprises the sequence of SEQ ID NO: 14.

30. The δ1 γδ T cell of claim 3, wherein the IL-15 in c comprises the sequence of SEQ ID NO: 14 operably linked to a secretion signal sequence of SEQ ID NO:12, or wherein the IL-15 comprises the sequence of SEQ ID NO: 14 operably linked to a secretion signal sequence of SEQ ID NO: 26.

31. The δ1 γδ T cell of claim 3, wherein the secreted common gamma chain interleukin in d is IL-15.

32. The δ1 γδ T cell of claim 3, wherein the multicistronic linker region comprises a sequence of any one of SEQ ID NOs: 15-17, 25, or 27-30, or a combination thereof, or encodes an internal ribosome entry site, e.g., SEQ ID NO: 31 or 32.

33. The δ1 γδ T cell of claim 6, wherein the secretion signal in a comprise SEQ ID NO: 12.

34. The method of claim 12, wherein the retroviral transduction is gammaretroviral transduction.

35. The method of claim 18, further comprising administering IL-2.

36. The method of claim 18, further comprising administering IL-15.

\* \* \* \* \*

SEQUENCE LISTING

```
<160> NUMBER OF SEQ ID NOS: 45

<210> SEQ ID NO 1
<211> LENGTH: 39
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Pro Thr Pro Ala Pro Thr Ile Ala Ser Gln Pro Leu Ser Leu Arg Pro
1               5                   10                  15

Glu Ala Cys Arg Pro Ala Ala Gly Gly Ala Val His Thr Arg Gly Leu
            20                  25                  30

Asp Phe Ala Cys Asp Ile Tyr
        35

<210> SEQ ID NO 2
<211> LENGTH: 47
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr
            35                  40                  45

<210> SEQ ID NO 3
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 3

Ile Trp Ala Pro Leu Ala Gly Thr Cys Gly Val Leu Leu Leu Ser Leu
1               5                   10                  15

Val Ile Thr Leu Tyr Cys
            20

<210> SEQ ID NO 4
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 5
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 6

-continued

```
<211> LENGTH: 42
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 7
<211> LENGTH: 48
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Gln Arg Arg Lys Tyr Arg Ser Asn Lys Gly Glu Ser Pro Val Glu Pro
1               5                   10                  15

Ala Glu Pro Cys His Tyr Ser Cys Pro Arg Glu Glu Glu Gly Ser Thr
            20                  25                  30

Ile Pro Ile Gln Glu Asp Tyr Arg Lys Pro Glu Pro Ala Cys Ser Pro
        35                  40                  45

<210> SEQ ID NO 8
<211> LENGTH: 487
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Met Ser Val Pro Thr Gln Val Leu Gly Leu Leu Leu Leu Trp Leu Thr
1               5                   10                  15

Asp Ala Arg Cys Asp Ile Gln Met Thr Gln Ser Pro Ser Ser Leu Ser
            20                  25                  30

Ala Ser Val Gly Asp Arg Val Thr Ile Thr Cys Lys Ala Ser Gln Asp
        35                  40                  45

Ile His Asn Tyr Ile Ala Trp Tyr Gln Gln Lys Pro Gly Lys Ala Pro
    50                  55                  60

Lys Leu Leu Ile His Tyr Thr Ser Thr Leu Gln Pro Gly Val Pro Ser
65                  70                  75                  80

Arg Phe Ser Gly Ser Gly Ser Gly Thr Asp Phe Thr Phe Thr Ile Ser
                85                  90                  95

Ser Leu Gln Pro Glu Asp Ile Ala Thr Tyr Tyr Cys Leu Gln Tyr Asp
            100                 105                 110

Asn Leu Trp Thr Phe Gly Gln Gly Thr Lys Val Glu Ile Lys Arg Gly
        115                 120                 125

Gly Gly Gly Ser Gly Gly Gly Gly Ser Gly Gly Gly Gly Gln Ile Thr
    130                 135                 140
```

-continued

```
Leu Lys Glu Ser Gly Pro Thr Leu Val Lys Pro Thr Gln Thr Leu Thr
145             150                 155                 160

Leu Thr Cys Thr Phe Ser Gly Phe Ser Leu Ser Thr Ser Gly Met Gly
                165                 170                 175

Val Ser Trp Ile Arg Gln Pro Pro Gly Lys Ala Leu Glu Trp Leu Ala
            180                 185                 190

His Ile Tyr Trp Asp Asp Asp Lys Arg Tyr Asn Pro Ser Leu Lys Ser
            195                 200                 205

Arg Leu Thr Ile Thr Lys Asp Thr Ser Lys Asn Gln Val Val Leu Thr
        210                 215                 220

Met Thr Asn Met Asp Pro Val Asp Thr Ala Thr Tyr Tyr Cys Ala Arg
225                 230                 235                 240

Lys Asp Tyr Gly Ser Ser Phe Tyr Ala Met His Tyr Trp Gly Gln Gly
                245                 250                 255

Thr Leu Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
            275                 280                 285

Ala Cys Arg Pro Ala Ala Gly Gly Ala Val His Thr Arg Gly Leu Asp
        290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
            355                 360                 365

Glu Gly Gly Cys Glu Leu Arg Val Lys Phe Ser Arg Ser Ala Asp Ala
        370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Gln Arg Arg Lys Asn Pro Gln Glu Gly
            420                 425                 430

Leu Tyr Asn Glu Leu Gln Lys Asp Lys Met Ala Glu Ala Tyr Ser Glu
            435                 440                 445

Ile Gly Met Lys Gly Glu Arg Arg Arg Gly Lys Gly His Asp Gly Leu
        450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485
```

<210> SEQ ID NO 9
<211> LENGTH: 1464
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 9
atgtccgtgc ctacccaggt gctgggcctg ctgctgctgt ggctgaccga cgccagatgc      60

```
gacatccaga tgacccagtc tccatcctcc ctgtctgcat ctgtaggaga cagagtcacc       120
atcacttgca aggcgagtca ggacattcac aactatatag cttggtatca gcagaaacca       180
gggaaagccc ctaagctcct gatccactat acatccactt tgcaaccagg ggtcccatca       240
aggttcagtg gaagtggatc tgggacagat tttactttca ccatcagcag cctgcagcct       300
gaagatattg caacatatta ctgtctacag tatgataatc tctggacgtt cggtcaaggc       360
accaaggtgg aaatcaaacg gggtggaggt ggatctggag gaggaggatc cggtggagga       420
ggtcagatca ccttgaagga gtctggtcct acgctggtga aacccacaca gaccctcacg       480
ctgacctgca ccttctctgg gttctcactc agcactagtg gaatgggtgt gtcctggatc       540
cgtcagcccc caggaaaggc cctggagtgg cttgcacaca tttattggga tgatgataag       600
cgctacaacc catctctgaa gagcaggctc accatcacca aggacacctc caaaaaccag       660
gtggtcctta caatgaccaa catggaccct gtggacacag ccacatatta ctgtgcacga       720
aaggactacg gtagtagctt ctatgctatg cactactggg gtcaaggaac cctagtcacc       780
gtgtcgagta ccacgacgcc agcgccgcga ccaccaacac cggcgcccac catcgcgtcg       840
cagcccctgt ccctgcgccc agaggcgtgc cggccagcgg cggggggcgc agtgcacacg       900 aggggggctgg acttcgcctg tgatatctac atctgggcgc ccttggccgg gacttgtggg       960
gtccttctcc tgtcactggt tatcacccct tactgcaaac ggggcagaaa gaaactcctg      1020
tatatattca aacaaccatt tatgagacca gtacaaacta ctcaagagga agatggctgt      1080
agctgccgat ttccagaaga agaagaagga ggatgtgaac tgagagtgaa gttcagcagg      1140
agcgcagacg cccccgcgta ccagcagggc cagaaccagc tctataacga gctcaatcta      1200
ggacgaagag aggagtacga tgttttggac aagagacgtg gccgggaccc tgagatgggg      1260
ggaaagccgc agagaaggaa gaaccctcag gaaggcctgt acaatgaact gcagaaagat      1320
aagatggcgg aggcctacag tgagattggg atgaaaggcg agcgccggag gggcaagggg      1380
cacgatggcc tttaccaggg tctcagtaca gccaccaagg acacctacga cgcccttcac      1440
atgcaggccc tgcccctcg ctaa                                              1464
```

<210> SEQ ID NO 10
<211> LENGTH: 135
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 10

```
accaccaccc ctgcaccaag gcccccgact cccgcgccca ccatcgcgtc acagcctctt        60
agcctgcgac cggaagcatg cagaccagct gccgggggggg ccgtgcatac gagaggtttg      120
gacttcgcct gcgat                                                       135
```

<210> SEQ ID NO 11
<211> LENGTH: 135
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 11

-continued

```
accacgacgc cagcgccgcg accaccaaca ccggcgccca ccatcgcgtc gcagcccctg          60
tccctgcgcc cagaggcgtg ccggccagcg gcggggggcg cagtgcacac gagggggctg         120
gacttcgcct gtgat                                                          135
```

```
<210> SEQ ID NO 12
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Met Ala Leu Pro Val Thr Ala Leu Leu Leu Pro Leu Ala Leu Leu Leu
1               5                   10                  15

His Ala Ala Arg Pro
            20

<210> SEQ ID NO 13

<400> SEQUENCE: 13

000

<210> SEQ ID NO 14
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
        50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 15
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Ser Gly Ser Gly Ala Thr Asn Phe Ser Leu Leu Lys Gln Ala Gly Asp
```

-continued

```
1               5              10              15

Val Glu Glu Asn Pro Gly Pro
            20

<210> SEQ ID NO 16
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Arg Ala Lys Arg
1

<210> SEQ ID NO 17
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Arg Ala Lys Arg Ser Gly Ser Gly Ala Thr Asn Phe Ser Leu Leu Lys
1               5              10              15

Gln Ala Gly Asp Val Glu Glu Asn Pro Gly Pro
            20                  25

<210> SEQ ID NO 18
<211> LENGTH: 649
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Met Ser Val Pro Thr Gln Val Leu Gly Leu Leu Leu Leu Trp Leu Thr
1               5              10              15

Asp Ala Arg Cys Asp Ile Gln Met Thr Gln Ser Pro Ser Ser Leu Ser
            20                  25                  30

Ala Ser Val Gly Asp Arg Val Thr Ile Thr Cys Lys Ala Ser Gln Asp
        35                  40                  45

Ile His Asn Tyr Ile Ala Trp Tyr Gln Gln Lys Pro Gly Lys Ala Pro
    50                  55                  60

Lys Leu Leu Ile His Tyr Thr Ser Thr Leu Gln Pro Gly Val Pro Ser
65                  70                  75                  80

Arg Phe Ser Gly Ser Gly Ser Gly Thr Asp Phe Thr Phe Thr Ile Ser
                85                  90                  95

Ser Leu Gln Pro Glu Asp Ile Ala Thr Tyr Tyr Cys Leu Gln Tyr Asp
            100                 105                 110

Asn Leu Trp Thr Phe Gly Gln Gly Thr Lys Val Glu Ile Lys Arg Gly
        115                 120                 125

Gly Gly Gly Ser Gly Gly Gly Ser Gly Gly Gly Gln Ile Thr
    130                 135                 140

Leu Lys Glu Ser Gly Pro Thr Leu Val Lys Pro Thr Gln Thr Leu Thr
145                 150                 155                 160
```

-continued

```
Leu Thr Cys Thr Phe Ser Gly Phe Ser Leu Ser Thr Ser Gly Met Gly
            165                 170                 175

Val Ser Trp Ile Arg Gln Pro Pro Gly Lys Ala Leu Glu Trp Leu Ala
            180                 185                 190

His Ile Tyr Trp Asp Asp Asp Lys Arg Tyr Asn Pro Ser Leu Lys Ser
            195                 200                 205

Arg Leu Thr Ile Thr Lys Asp Thr Ser Lys Asn Gln Val Val Leu Thr
    210                 215                 220

Met Thr Asn Met Asp Pro Val Asp Thr Ala Thr Tyr Tyr Cys Ala Arg
225                 230                 235                 240

Lys Asp Tyr Gly Ser Ser Phe Tyr Ala Met His Tyr Trp Gly Gln Gly
                245                 250                 255

Thr Leu Val Thr Val Ser Ser Thr Thr Thr Pro Ala Pro Arg Pro Pro
                260                 265                 270

Thr Pro Ala Pro Thr Ile Ala Ser Gln Pro Leu Ser Leu Arg Pro Glu
                275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
                340                 345                 350

Thr Thr Gln Glu Glu Asp Gly Cys Ser Cys Arg Phe Pro Glu Glu Glu
                355                 360                 365

Glu Gly Gly Cys Glu Leu Arg Val Lys Phe Ser Arg Ser Ala Asp Ala
    370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Gln Arg Arg Lys Asn Pro Gln Glu Gly
                420                 425                 430

Leu Tyr Asn Glu Leu Gln Lys Asp Lys Met Ala Glu Ala Tyr Ser Glu
                435                 440                 445

Ile Gly Met Lys Gly Glu Arg Arg Arg Gly Lys Gly His Asp Gly Leu
    450                 455                 460

Tyr Gln Gly Leu Ser Thr Ala Thr Lys Asp Thr Tyr Asp Ala Leu His
465                 470                 475                 480

Met Gln Ala Leu Pro Pro Arg Arg Ala Lys Arg Ser Gly Ser Gly Ala
                485                 490                 495

Thr Asn Phe Ser Leu Leu Lys Gln Ala Gly Asp Val Glu Glu Asn Pro
                500                 505                 510

Gly Pro Met Ala Leu Pro Val Thr Ala Leu Leu Leu Pro Leu Ala Leu
                515                 520                 525

Leu Leu His Ala Ala Arg Pro Asn Trp Val Asn Val Ile Ser Asp Leu
    530                 535                 540

Lys Lys Ile Glu Asp Leu Ile Gln Ser Met His Ile Asp Ala Thr Leu
545                 550                 555                 560

Tyr Thr Glu Ser Asp Val His Pro Ser Cys Lys Val Thr Ala Met Lys
                565                 570                 575
```

```
Cys Phe Leu Leu Glu Leu Gln Val Ile Ser Leu Glu Ser Gly Asp Ala
            580             585                 590

Ser Ile His Asp Thr Val Glu Asn Leu Ile Ile Leu Ala Asn Asn Ser
        595                 600                 605

Leu Ser Ser Asn Gly Asn Val Thr Glu Ser Gly Cys Lys Glu Cys Glu
        610             615                 620

Glu Leu Glu Glu Lys Asn Ile Lys Glu Phe Leu Gln Ser Phe Val His
625             630                 635                 640

Ile Val Gln Met Phe Ile Asn Thr Ser
            645
```

<210> SEQ ID NO 19
<211> LENGTH: 1950
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 19

```
atgtccgtgc ctacccaggt gctgggcctg ctgctgctgt ggctgaccga cgccagatgc      60
gacatccaga tgacccagtc tccatcctcc ctgtctgcat ctgtaggaga cagagtcacc     120
atcacttgca aggcgagtca ggacattcac aactatatag cttggtatca gcagaaacca     180
gggaaagccc ctaagctcct gatccactat acatccactt tgcaaccagg ggtcccatca     240
aggttcagtg gaagtggatc tgggacagat tttactttca ccatcagcag cctgcagcct     300
gaagatattg caacatatta ctgtctacag tatgataatc tctggacgtt cggtcaaggc     360
accaaggtgg aaatcaaacg gggtggaggt ggatctggag gaggaggatc cggtggagga     420
ggtcagatca ccttgaagga gtctggtcct acgctggtga aacccacaca gaccctcacg     480
ctgacctgca ccttctctgg gttctcactc agcactagtg aatgggtgt gtcctggatc     540 cgtcagcccc caggaaaggc cctggagtgg cttgcacaca tttattggga tgatgataag     600
cgctacaacc catctctgaa gagcaggctc accatcacca aggacacctc caaaaaccag     660
gtggtcctta caatgaccaa catggaccct gtggacacag ccacatatta ctgtgcacga     720
aaggactacg gtagtagctt ctatgctatg cactactggg gtcaaggaac cctagtcacc     780
gtgtcgagta ccaccacccc tgcaccaagg cccccgactc ccgcgccac catcgcgtca     840 cagcctctta gcctgcgacc ggaagcatgc agaccagctg ccgggggggc cgtgcatacg     900
agaggtttgg acttcgcctg cgatatctac atctgggcgc ccttggccgg acttgtgggg     960
gtccttctcc tgtcactggt tatcacccctt tactgcaaac ggggcagaaa gaaactcctg    1020
tatatattca acaaccatt tatgagacca gtacaaacta ctcaagagga agatggctgt    1080
agctgccgat ttccagaaga agaagaagga ggatgtgaac tgagagtgaa gttcagcagg    1140
agcgcagacg cccccgcgta ccagcagggc cagaaccagc tctataacga gctcaatcta    1200
ggacgaagag aggagtacga tgttttggac aagagacgtg gccgggaccc tgagatgggg    1260
ggaaagccgc agagaaggaa gaaccctcag gaaggcctgt acaatgaact gcagaaagat    1320
aagatggcgg aggcctacag tgagattggg atgaaaggcg agcgccggag gggcaagggg    1380
cacgatggcc tttaccaggg tctcagtaca gccaccaagg acacctacga cgcccttcac    1440
atgcaggccc tgcccccctcg ccgcgcgaag cgatcaggca gcgggcgac aaatttcagc    1500 cttctgaaac aagcaggcga cgtggaagaa aaccccggtc caatggcctt accagtgacc    1560
```

-continued

```
gccttgctcc tgccgctggc cttgctgctc cacgccgcca ggccgaactg ggtgaatgta   1620
ataagtgatt tgaaaaaaat tgaagatctt attcaatcta tgcatattga tgctacttta   1680
tatacggaaa gtgatgttca ccccagttgc aaagtaacag caatgaagtg ctttctcttg   1740
gagttacaag ttatttcact tgagtccgga gatgcaagta ttcatgatac agtagaaaat   1800
ctgatcatcc tagcaaacaa cagtttgtct tctaatggga atgtaacaga atctggatgc   1860
aaagaatgtg aggaactgga ggaaaaaaat attaaagaat ttttgcagag ttttgtacat   1920
attgtccaaa tgttcatcaa cacttcttga                                    1950
```

<210> SEQ ID NO 20
<211> LENGTH: 485
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 20

```
Met Ser Val Pro Thr Gln Val Leu Gly Leu Leu Leu Leu Trp Leu Thr
1               5                   10                  15

Asp Ala Arg Cys Gln Val Gln Leu Val Gln Ser Gly Ala Glu Val Lys
            20                  25                  30

Lys Pro Gly Ala Ser Val Lys Val Ser Cys Lys Ala Ser Gly Tyr Thr
        35                  40                  45

Phe Thr Asp Tyr Glu Met His Trp Val Arg Gln Ala Pro Gly Gln Gly
    50                  55                  60

Leu Glu Trp Met Gly Ala Leu Asp Pro Lys Thr Gly Asp Thr Ala Tyr
65                  70                  75                  80

Ser Gln Lys Phe Lys Gly Arg Val Thr Leu Thr Ala Asp Lys Ser Thr
                85                  90                  95

Ser Thr Ala Tyr Met Glu Leu Ser Ser Leu Thr Ser Glu Asp Thr Ala
            100                 105                 110

Val Tyr Tyr Cys Thr Arg Phe Tyr Ser Tyr Thr Tyr Trp Gly Gln Gly
        115                 120                 125

Thr Leu Val Thr Val Ser Ser Gly Gly Gly Gly Ser Gly Gly Gly Gly
    130                 135                 140

Ser Gly Gly Gly Gly Asp Val Val Met Thr Gln Ser Pro Leu Ser Leu
145                 150                 155                 160

Pro Val Thr Pro Gly Glu Pro Ala Ser Ile Ser Cys Arg Ser Ser Gln
                165                 170                 175

Ser Leu Val His Ser Asn Arg Asn Thr Tyr Leu His Trp Tyr Leu Gln
            180                 185                 190

Lys Pro Gly Gln Ser Pro Gln Leu Leu Ile Tyr Lys Val Ser Asn Arg
        195                 200                 205

Phe Ser Gly Val Pro Asp Arg Phe Ser Gly Ser Gly Ser Gly Thr Asp
    210                 215                 220

Phe Thr Leu Lys Ile Ser Arg Val Glu Ala Glu Asp Val Gly Val Tyr
225                 230                 235                 240

Tyr Cys Ser Gln Asn Thr His Val Pro Pro Thr Phe Gly Gln Gly Thr
                245                 250                 255

Lys Leu Glu Ile Lys Thr Thr Thr Pro Ala Pro Arg Pro Pro Thr Pro
            260                 265                 270

Ala Pro Thr Ile Ala Ser Gln Pro Leu Ser Leu Arg Pro Glu Ala Cys
        275                 280                 285
```

```
Arg Pro Ala Ala Gly Gly Ala Val His Thr Arg Gly Leu Asp Phe Ala
    290                 295                 300

Cys Asp Ile Tyr Ile Trp Ala Pro Leu Ala Gly Thr Cys Gly Val Leu
305                 310                 315                 320

Leu Leu Ser Leu Val Ile Thr Leu Tyr Cys Lys Arg Gly Arg Lys Lys
                325                 330                 335

Leu Leu Tyr Ile Phe Lys Gln Pro Phe Met Arg Pro Val Gln Thr Thr
                340                 345                 350

Gln Glu Glu Asp Gly Cys Ser Cys Arg Phe Pro Glu Glu Glu Glu Gly
        355                 360                 365

Gly Cys Glu Leu Arg Val Lys Phe Ser Arg Ser Ala Asp Ala Pro Ala
    370                 375                 380

Tyr Gln Gln Gly Gln Asn Gln Leu Tyr Asn Glu Leu Asn Leu Gly Arg
385                 390                 395                 400

Arg Glu Glu Tyr Asp Val Leu Asp Lys Arg Arg Gly Arg Asp Pro Glu
                405                 410                 415

Met Gly Gly Lys Pro Gln Arg Arg Lys Asn Pro Gln Glu Gly Leu Tyr
                420                 425                 430

Asn Glu Leu Gln Lys Asp Lys Met Ala Glu Ala Tyr Ser Glu Ile Gly
        435                 440                 445

Met Lys Gly Glu Arg Arg Arg Gly Lys Gly His Asp Gly Leu Tyr Gln
    450                 455                 460

Gly Leu Ser Thr Ala Thr Lys Asp Thr Tyr Asp Ala Leu His Met Gln
465                 470                 475                 480

Ala Leu Pro Pro Arg
                485

<210> SEQ ID NO 21
<211> LENGTH: 1458
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 21
atgtccgtgc ctacccaggt gctgggcctg ctgctgctgt ggctgaccga cgccagatgc      60
caagtgcagc tggtccagag cggcgccgag gtgaaaaagc ctggcgccag cgtgaaggtg     120
tcctgcaagg cctctggcta caccttcacc gactacgaga tgcactgggt gcggcaggcc     180
cctggacagg gcctggaatg gatgggcgct ctggacccca gaccggcga caccgcttat     240 agccagaagt tcaagggcag agtgaccctg acagctgata gagcacaag caccgcctac     300 atggaactga gcagcctgac cagcgaggac accgccgtgt actactgcac cagattctac     360
agctacacct actggggcca ggggaccctg gtgacagtgt ctagcggtgg aggtggatct     420
ggaggaggag gatccggtgg aggaggtgat gtggtgatga cccagagccc tctgagcctg     480
cctgtgaccc ctggagagcc tgccagcatc agctgcagaa gcagccaatc tctggtgcac     540
agcaaccgga acatatacct gcactggtac ctgcagaaac ctggccagag ccccagctg     600 ctgatctaca aggtgtccaa cagattcagc ggcgtgcctg atagattcag cggatctggc     660
agcggcaccg acttcaccct gaagatctct agagtggaag ccgaggacgt gggcgtgtac     720
tactgcagcc agaacaccca cgtgcccccc accttcggcc agggcacaaa gctggaaatc     780
aagaccacga cgccagcgcc gcgaccacca acaccggcgc ccaccatcgc gtcgcagccc     840
```

```
ctgtccctgc gcccagaggc gtgccggcca gcggcggggg gcgcagtgca cacgaggggg    900
ctggacttcg cctgtgatat ctacatctgg gcgcccttgg ccgggacttg tggggtcctt    960
ctcctgtcac tggttatcac cctttactgc aaacggggca gaaagaaact cctgtatata   1020
ttcaaacaac catttatgag accagtacaa actactcaag aggaagatgg ctgtagctgc   1080
cgatttccag aagaagaaga aggaggatgt gaactgagag tgaagttcag caggagcgca   1140
gacgcccccg cgtaccagca gggccagaac cagctctata cgagctcaa tctaggacga    1200 agagaggagt acgatgtttt ggacaagaga cgtggccggg accctgagat ggggggaaag   1260
ccgcagagaa ggaagaaccc tcaggaaggc ctgtacaatg aactgcagaa agataagatg   1320
gcggaggcct acagtgagat tgggatgaaa ggcgagcgcc ggaggggcaa ggggcacgat   1380
ggcctttacc agggtctcag tacagccacc aaggacacct acgacgccct tcacatgcag   1440
gccctgcccc ctcgctaa                                                 1458
```

<210> SEQ ID NO 22
<211> LENGTH: 642
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 22

```
Met Ser Val Pro Thr Gln Val Leu Gly Leu Leu Leu Leu Trp Leu Thr
1               5                   10                  15

Asp Ala Arg Cys Gln Val Gln Leu Val Gln Ser Gly Ala Glu Val Lys
            20                  25                  30

Lys Pro Gly Ala Ser Val Lys Val Ser Cys Lys Ala Ser Gly Tyr Thr
        35                  40                  45

Phe Thr Asp Tyr Glu Met His Trp Val Arg Gln Ala Pro Gly Gln Gly
    50                  55                  60

Leu Glu Trp Met Gly Ala Leu Asp Pro Lys Thr Gly Asp Thr Ala Tyr
65                  70                  75                  80

Ser Gln Lys Phe Lys Gly Arg Val Thr Leu Thr Ala Asp Lys Ser Thr
                85                  90                  95

Ser Thr Ala Tyr Met Glu Leu Ser Ser Leu Thr Ser Glu Asp Thr Ala
            100                 105                 110

Val Tyr Tyr Cys Thr Arg Phe Tyr Ser Tyr Thr Tyr Trp Gly Gln Gly
        115                 120                 125

Thr Leu Val Thr Val Ser Ser Gly Gly Gly Ser Gly Gly Gly Gly
    130                 135                 140

Ser Gly Gly Gly Gly Asp Val Val Met Thr Gln Ser Pro Leu Ser Leu
145                 150                 155                 160

Pro Val Thr Pro Gly Glu Pro Ala Ser Ile Ser Cys Arg Ser Ser Gln
                165                 170                 175

Ser Leu Val His Ser Asn Arg Asn Thr Tyr Leu His Trp Tyr Leu Gln
            180                 185                 190

Lys Pro Gly Gln Ser Pro Gln Leu Leu Ile Tyr Lys Val Ser Asn Arg
        195                 200                 205

Phe Ser Gly Val Pro Asp Arg Phe Ser Gly Ser Gly Ser Gly Thr Asp
    210                 215                 220

Phe Thr Leu Lys Ile Ser Arg Val Glu Ala Glu Asp Val Gly Val Tyr
225                 230                 235                 240
```

-continued

```
Tyr Cys Ser Gln Asn Thr His Val Pro Pro Thr Phe Gly Gln Gly Thr
                245                 250                 255

Lys Leu Glu Ile Lys Thr Thr Thr Pro Ala Pro Arg Pro Pro Thr Pro
                260                 265                 270

Ala Pro Thr Ile Ala Ser Gln Pro Leu Ser Leu Arg Pro Glu Ala Cys
                275                 280                 285

Arg Pro Ala Ala Gly Gly Ala Val His Thr Arg Gly Leu Asp Phe Ala
                290                 295                 300

Cys Asp Ile Tyr Ile Trp Ala Pro Leu Ala Gly Thr Cys Gly Val Leu
305                 310                 315                 320

Leu Leu Ser Leu Val Ile Thr Leu Tyr Cys Lys Arg Gly Arg Lys Lys
                325                 330                 335

Leu Leu Tyr Ile Phe Lys Gln Pro Phe Met Arg Pro Val Gln Thr Thr
                340                 345                 350

Gln Glu Glu Asp Gly Cys Ser Cys Arg Phe Pro Glu Glu Glu Glu Gly
                355                 360                 365

Gly Cys Glu Leu Arg Val Lys Phe Ser Arg Ser Ala Asp Ala Pro Ala
                370                 375                 380

Tyr Gln Gln Gly Gln Asn Gln Leu Tyr Asn Glu Leu Asn Leu Gly Arg
385                 390                 395                 400

Arg Glu Glu Tyr Asp Val Leu Asp Lys Arg Arg Gly Arg Asp Pro Glu
                405                 410                 415

Met Gly Gly Lys Pro Gln Arg Arg Lys Asn Pro Gln Glu Gly Leu Tyr
                420                 425                 430

Asn Glu Leu Gln Lys Asp Lys Met Ala Glu Ala Tyr Ser Glu Ile Gly
                435                 440                 445

Met Lys Gly Glu Arg Arg Arg Gly Lys Gly His Asp Gly Leu Tyr Gln
                450                 455                 460

Gly Leu Ser Thr Ala Thr Lys Asp Thr Tyr Asp Ala Leu His Met Gln
465                 470                 475                 480

Ala Leu Pro Pro Arg Gly Ser Gly Ala Thr Asn Phe Ser Leu Leu Lys
                485                 490                 495

Gln Ala Gly Asp Val Glu Glu Asn Pro Gly Pro Met Ala Leu Pro Val
                500                 505                 510

Thr Ala Leu Leu Leu Pro Leu Ala Leu Leu Leu His Ala Ala Arg Pro
                515                 520                 525

Asn Trp Val Asn Val Ile Ser Asp Leu Lys Lys Ile Glu Asp Leu Ile
                530                 535                 540

Gln Ser Met His Ile Asp Ala Thr Leu Tyr Thr Glu Ser Asp Val His
545                 550                 555                 560

Pro Ser Cys Lys Val Thr Ala Met Lys Cys Phe Leu Leu Glu Leu Gln
                565                 570                 575

Val Ile Ser Leu Glu Ser Gly Asp Ala Ser Ile His Asp Thr Val Glu
                580                 585                 590

Asn Leu Ile Ile Leu Ala Asn Asn Ser Leu Ser Ser Asn Gly Asn Val
                595                 600                 605

Thr Glu Ser Gly Cys Lys Glu Cys Glu Glu Leu Glu Glu Lys Asn Ile
                610                 615                 620

Lys Glu Phe Leu Gln Ser Phe Val His Ile Val Gln Met Phe Ile Asn
625                 630                 635                 640

Thr Ser
```

```
<210> SEQ ID NO 23
<211> LENGTH: 1929
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 23
atgtccgtgc ctacccaggt gctgggcctg ctgctgctgt ggctgaccga cgccagatgc      60
caagtgcagc tggtccagag cggcgccgag gtgaaaaagc ctggcgccag cgtgaaggtg     120
tcctgcaagg cctctggcta caccttcacc gactacgaga tgcactgggt gcggcaggcc     180
cctggacagg gcctggaatg gatgggcgct ctggacccca gaccggcga caccgcttat     240 agccagaagt tcaagggcag agtgaccctg acagctgata gagcacaag caccgcctac     300 atggaactga gcagcctgac cagcgaggac accgccgtgt actactgcac cagattctac     360
agctacacct actggggcca ggggacccta gtgacagtgt ctagcggtgg aggtggatct     420
ggaggaggag gatccggtgg aggaggtgat gtggtgatga cccagagccc tctgagcctg     480
cctgtgaccc ctggagagcc tgccagcatc agctgcagaa gcagccaatc tctggtgcac     540
agcaaccgga acacatacct gcactggtac ctgcagaaac ctggccagag ccccagctg     600 ctgatctaca aggtgtccaa cagattcagc ggcgtgcctg atagattcag cggatctggc     660
agcggcaccg acttcaccct gaagatctct agagtggaag ccgaggacgt gggcgtgtac     720
tactgcagcc agaacaccca cgtgcccccc accttcggcc agggcacaaa gctggaaatc     780
aagaccacga cgccagcgcc gcgaccacca acaccggcgc ccaccatcgc gtcgcagccc     840
ctgtccctgc gcccagaggc gtgccggcca gcggcggggg gcgcagtgca cacgaggggg     900
ctggacttcg cctgtgatat ctacatctgg gcgcccttgg ccgggacttg tggggtcctt     960
ctcctgtcac tggttatcac ccttttactgc aaacggggca gaaagaaact cctgtatata    1020
ttcaaacaac catttatgag accagtacaa actactcaag aggaagatgg ctgtagctgc    1080
cgatttccag aagaagaaga aggaggatgt gaactgagag tgaagttcag caggagcgca    1140
gacgcccccg cgtaccagca gggccagaac cagctctata cgagctcaa tctaggacga    1200 agagaggagt acgatgtttt ggacaagaga cgtggccggg accctgagat gggggggaaag    1260 ccgcagagaa ggaagaaccc tcaggaaggc ctgtacaatg aactgcagaa agataagatg    1320
gcggaggcct acagtgagat tgggatgaaa ggcgagcgcc ggaggggcaa ggggcacgat    1380
ggcctttacc agggtctcag tacagccacc aaggacacct acgacgccct tcacatgcag    1440
gccctgcccc ctcgcggtag cggggctacg aacttctccc ttcttaaaca agcgggagac    1500
gtggaagaaa atcccggacc tatggcctta ccagtgaccg ccttgctcct gccgctggcc    1560
ttgctgctcc acgccgccag gccgaactgg gtgaatgtaa taagtgattt gaaaaaaatt    1620
gaagatctta ttcaatctat gcatattgat gctactttat atacggaaag tgatgttcac    1680
cccagttgca aagtaacagc aatgaagtgc tttctcttgg agttacaagt tatttcactt    1740
gagtccggag atgcaagtat tcatgataca gtagaaaatc tgatcatcct agcaaacaac    1800
agtttgtctt ctaatgggaa tgtaacagaa tctggatgca agaatgtga ggaactggag    1860 gaaaaaaata ttaaagaatt tttgcagagt tttgtacata ttgtccaaat gttcatcaac    1920
acttcttga                                                            1929

<210> SEQ ID NO 24
```

-continued

```
<211> LENGTH: 1929
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 24
atgtccgtgc ctacccaggt gctgggcctg ctgctgctgt ggctgaccga cgccagatgc      60
caagtgcagc tggtccagag cggcgccgag gtgaaaaagc ctggcgccag cgtgaaggtg     120
tcctgcaagg cctctggcta caccttcacc gactacgaga tgcactgggt gcggcaggcc     180
cctggacagg gcctggaatg gatgggcgct ctggacccca agaccggcga caccgcttat     240
agccagaagt tcaagggcag agtgaccctg acagctgata gagcacaag caccgcctac     300 atggaactga gcagcctgac cagcgaggac accgccgtgt actactgcac cagattctac     360
agctacacct actggggcca ggggaccctg gtgacagtgt ctagcggtgg aggtggatct     420
ggaggaggag gatccggtgg aggaggtgat gtggtgatga cccagagccc tctgagcctg     480
cctgtgaccc ctggagagcc tgccagcatc agctgcagaa gcagccaatc tctggtgcac     540
agcaaccgga acacatacct gcactggtac ctgcagaaac ctggccagag cccccagctg     600
ctgatctaca aggtgtccaa cagattcagc ggcgtgcctg atagattcag cggatctggc     660
agcggcaccg acttcaccct gaagatctct agagtggaag ccgaggacgt gggcgtgtac     720
tactgcagcc agaacaccca cgtgcccccc accttcggcc agggcacaaa gctggaaatc     780
aagaccacga cgccagcgcc gcgaccacca acaccggcgc ccaccatcgc gtcgcagccc     840
ctgtccctgc gcccagaggc gtgccggcca gcggcggggg gcgcagtgca cacgaggggg     900
ctggacttcg cctgtgatat ctacatctgg gcgcccttgg ccgggacttg tggggtcctt     960
ctcctgtcac tggttatcac cctttactgc aaacggggca gaaagaaact cctgtatata    1020
ttcaaacaac catttatgag accagtacaa actactcaag aggaagatgg ctgtagctgc    1080
cgatttccag aagaagaaga aggaggatgt gaactgagag tgaagttcag caggagcgca    1140
gacgcccccg cgtaccagca gggccagaac cagctctata cgagctcaa tctaggacga    1200 agagaggagt acgatgtttt ggacaagaga cgtggccggg accctgagat ggggggaaag    1260
ccgcagagaa ggaagaaccc tcaggaaggc ctgtacaatg aactgcagaa agataagatg    1320
gcggaggcct acagtgagat tgggatgaaa ggcgagcgcc ggaggggcaa ggggcacgat    1380
ggcctttacc agggtctcag tacagccacc aaggacacct acgacgccct tcacatgcag    1440
gccctgcccc ctcgcggtag cggggctacg aacttctccc ttcttaaaca agcgggagac    1500
gtggaagaaa atcccggacc tatggcctta ccagtgaccg ccttgctcct gccgctggcc    1560
ttgctgctcc acgccgccag gccgaactgg gtgaatgtga tcagcgatct gaagaagatc    1620
gaggatctga tccagtccat gcacatcgat gccaccctgt ataccgagag cgatgtgcac    1680
cccagctgca aggtgaccgc catgaagtgc tttctgctgg agctgcaggt gatctccctg    1740
gagtccggag atgccagcat ccacgatacc gtggagaatc tgatcatcct ggccaacaac    1800
agcctgtcct ccaatggcaa tgtgaccgag tcgggatgca aggagtgcga ggagctggag    1860
gagaagaata tcaaggagtt tctgcagagc tttgtacata ttgtccaaat gttcatcaac    1920
acttcttga                                                            1929

<210> SEQ ID NO 25
<211> LENGTH: 22
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 26
<211> LENGTH: 48
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

<210> SEQ ID NO 27
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Ala Thr Asn Phe Ser Leu Leu Lys Gln Ala Gly Asp Val Glu Glu Asn
1               5                   10                  15

Pro Gly Pro

<210> SEQ ID NO 28
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Val Lys Gln Thr Leu Asn Asn Phe Asp Leu Leu Lys Leu Ala Gly Asp
1               5                   10                  15

Val Glu Ser Asn Pro Gly Pro
            20

<210> SEQ ID NO 29
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
```

```
      Synthetic peptide"

<400> SEQUENCE: 29

Gln Cys Thr Asn Tyr Ala Leu Leu Lys Leu Ala Gly Asp Val Glu Ser
1               5                   10                  15

Asn Pro Gly Pro
            20

<210> SEQ ID NO 30
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Glu Gly Arg Ser Leu Leu Thr Cys Gly Asp Val Glu Glu Asn Pro Gly
1               5                   10                  15

Pro

<210> SEQ ID NO 31
<211> LENGTH: 553
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 31
ctaacgttac tggccgaagc cgcttggaat aaggccggtg tgcgtttgtc tatatgttat      60
tttccaccat attgccgtct tttggcaatg tgagggcccg gaaacctggc cctgtcttct     120
tgacgagcat cctagggggt ctttcccctc tcgccaaagg aatgcaaggt ctgttgaatg     180
tcgtgaagga agcagttcct ctggaagctt cttgaagaca aacaacgtct gtagcgaccc     240
tttgcaggca gcggaacccc ccacctggcg acaggtgcct ctgcggccaa aagccacgtg     300
tataagatac acctgcaaag gcggcacaac cccagtgcca cgttgtgagt tggatagttg     360
tggaaagagt caaatggctc tcctcaagcg tattcaacaa ggggctgaag gatgcccaga     420
aggtacccca ttgtatggga tctgatctgg ggcctcggtg cacatgcttt acatgtgttt     480
agtcgaggtt aaaaaaacgt ctaggccccc cgaaccacgg ggacgtggtt ttcctttgaa     540
aaacacgatg ata                                                        553

<210> SEQ ID NO 32
<211> LENGTH: 461
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 32
agcaggtttc cccaactgac acaaaacgtg caacttgaaa ctccgcctgg tctttccagg      60
tctagagggg taacactttg tactgcgttt ggctccacgc tcgatccact ggcgagtgtt     120
agtaacagca ctgttgcttc gtagcggagc atgacggccg tgggaactcc tccttggtaa     180
caaggaccca cggggccaaa agccacgccc acacgggccc gtcatgtgtg caaccccagc     240
```

-continued

```
acggcgactt tactgcgaaa cccactttaa agtgacattg aaactggtac ccacacactg      300
gtgacaggct aaggatgccc ttcaggtacc ccgaggtaac acgcgacact cgggatctga      360
gaaggggact ggggcttcta taaaagcgct cggtttaaaa agcttctatg cctgaatagg      420
tgaccggagg tcggcacctt tcctttgcaa ttactgacca c                          461
```

```
<210> SEQ ID NO 33
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Thr Ser Gly Met Gly Val Ser
1               5

<210> SEQ ID NO 34
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

His Ile Tyr Trp Asp Asp Asp Lys Arg Tyr Asn Pro Ser Leu Lys Ser
1               5                   10                  15

<210> SEQ ID NO 35
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Lys Asp Tyr Gly Ser Ser Phe Tyr Ala Met His Tyr
1               5                   10

<210> SEQ ID NO 36
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Lys Ala Ser Gln Asp Ile His Asn Tyr Ile Ala
1               5                   10

<210> SEQ ID NO 37
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37
```

```
Tyr Thr Ser Thr Leu Gln Pro
1               5

<210> SEQ ID NO 38
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Leu Gln Tyr Asp Asn Leu Trp Thr
1               5

<210> SEQ ID NO 39
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Asp Tyr Glu Met His
1               5

<210> SEQ ID NO 40
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Gly Tyr Thr Phe Thr Asp Tyr Glu Met His
1               5                   10

<210> SEQ ID NO 41
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Ala Leu Asp Pro Lys Thr Gly Asp Thr Ala Tyr Ser Gln Lys Phe Lys
1               5                   10                  15

Gly

<210> SEQ ID NO 42
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Phe Tyr Ser Tyr Thr Tyr
```

-continued

```
1               5

<210> SEQ ID NO 43
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Arg Ser Ser Gln Ser Leu Val His Ser Asn Arg Asn Thr Tyr Leu His
1               5                   10                  15

<210> SEQ ID NO 44
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Lys Val Ser Asn Arg Phe Ser
1               5

<210> SEQ ID NO 45
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Ser Gln Asn Thr His Val Pro Pro Thr
1               5
```